United States Patent
Pagani et al.

(10) Patent No.: US 11,613,777 B2
(45) Date of Patent: Mar. 28, 2023

(54) NUCLEIC ACID EXTRACTION AND AMPLIFICATION CONTROLS AND METHODS OF USE THEREOF

(71) Applicant: LIFE TECHNOLOGIES CORPORATION, Carlsbad, CA (US)

(72) Inventors: Ioanna Pagani, Oakland, CA (US); Emily Zeringer, Buda, TX (US); Kelly Li, San Jose, CA (US); Boli Huang, Palo Alto, CA (US)

(*) Notice: Subject to any disclaimer, the term of this patent is extended or adjusted under 35 U.S.C. 154(b) by 97 days.

(21) Appl. No.: 15/687,046

(22) Filed: Aug. 25, 2017

(65) Prior Publication Data
US 2018/0073055 A1  Mar. 15, 2018

Related U.S. Application Data

(60) Provisional application No. 62/380,253, filed on Aug. 26, 2016, provisional application No. 62/380,291, filed on Aug. 26, 2016.

(51) Int. Cl.
| | |
|---|---|
| *C12Q 1/686* | (2018.01) |
| *C12Q 1/689* | (2018.01) |
| *C12Q 1/6851* | (2018.01) |
| *C12Q 1/70* | (2006.01) |
| *B01L 3/00* | (2006.01) |
| *C12Q 1/6806* | (2018.01) |
| *C12Q 1/6848* | (2018.01) |

(52) U.S. Cl.
CPC ............ *C12Q 1/686* (2013.01); *B01L 3/5085* (2013.01); *C12Q 1/6806* (2013.01); *C12Q 1/689* (2013.01); *C12Q 1/6848* (2013.01); *C12Q 1/6851* (2013.01); *C12Q 1/706* (2013.01); *B01L 2300/0819* (2013.01)

(58) Field of Classification Search
CPC .......... B01L 2300/0819; B01L 3/5085; C12Q 1/686; C12Q 1/6806; C12Q 1/6848; C12Q 1/6851; C12Q 1/689; C12Q 1/706
See application file for complete search history.

(56) References Cited

U.S. PATENT DOCUMENTS

| | | | |
|---|---|---|---|
| 6,358,679 B1* | 3/2002 | Heid | C12Q 1/686 435/5 |
| 2012/0190010 A1* | 7/2012 | Eickhoff | C12Q 1/6806 435/5 |
| 2017/0016059 A1* | 1/2017 | Lee | C12Q 1/6806 |
| 2017/0362640 A1 | 12/2017 | Pagani et al. | |

FOREIGN PATENT DOCUMENTS

| | | |
|---|---|---|
| CN | 101321877 | 4/2013 |
| CN | 103215248 | 5/2016 |
| EP | 3504342 A1 | 7/2019 |
| WO | 2015/103741 A1 | 7/2015 |

OTHER PUBLICATIONS

Stocher et al. (Journal of Clinical Virology 29 (2004) 171-178).*
Kalle et al. (Journal of Microbiological Methods 95 (2013) 285-294).*
Wang et al. (Theranostics, 2013; 3(6): 395-408).*
Pinheiro and Holliger (Trends in Biotechnology Jun. 2014, vol. 32, No. 6, p. 321-328).*
Pinheiro et al. (Science 336, 341-344 (2012)).*
Fu, Changlin, et al., "Hot Fusion: An Efficient Method to Clone Multiple DNA Fragments as Well as Inverted Repeats without Ligase", Plos One, vol. 9, No. 2, 2014, 1-20.
Maaroufi, Younes, et al., "Development of a multiple internal control for clinical diagnostic real-time amplification assays", FEMS Immunology & Medical Microbiology, vol. 48, No. 2, 2006, 183-191.
Nadkarni, Mangala, et al., "Determination of bacterial load by real-time PCR using a broad-range (universal) probe and primers set", Microbiology, 148, 2002, 237-266.
PCT/US2017/048680, International Search Report and Written Opinion dated Nov. 10, 2017, 13 pages.
Stocher, Markus, et al., "A convenient approach to the generation of multiple internal control DNA for a panel of real-time PCR assays", Journal of Virological Methods, vol. 108, No. 1, 2003, 1-8.
International Preliminary Report on Patentability for International Application No. PCT/US2017/048680 dated Feb. 26, 2019, 7 pages.
Chinese First Office Action for Chinese Application No. 201780052296. 3, dated Nov. 25, 2022, 6 pages.
Stöcher et al., "A convenient approach to the generation of multiple internal control DNA for a panel of real-time PCT assays," Journal of Virological Methods, (2003), pp. 1-8.

* cited by examiner

*Primary Examiner* — Robert H Havlin
(74) *Attorney, Agent, or Firm* — Workman Nydegger; Logan Christenson; John Guynn

(57) ABSTRACT

Nucleic acid reagents and corresponding methods of using the same for monitoring and evaluating nucleic acid extraction and amplification reactions.

25 Claims, 8 Drawing Sheets

Specification includes a Sequence Listing.

```
                         SEQUENCE LISTING

<160> NUMBER OF SEQ ID NOS: 34

<210> SEQ ID NO 1
<211> LENGTH: 18
<212> TYPE: DNA
<213> ORGANISM: Artificial Sequence
<220> FEATURE:
<223> OTHER INFORMATION: Synthetic DNA

<400> SEQUENCE: 1
gagcgtgtaa ctgttaaa                                                        18

<210> SEQ ID NO 2
<211> LENGTH: 18
<212> TYPE: DNA
<213> ORGANISM: Artificial Sequence
<220> FEATURE:
<223> OTHER INFORMATION: Synthetic DNA

<400> SEQUENCE: 2
tttgcataat gaatctga                                                        18

<210> SEQ ID NO 3
<211> LENGTH: 18
<212> TYPE: DNA
<213> ORGANISM: Artificial Sequence
<220> FEATURE:
<223> OTHER INFORMATION: Synthetic DNA

<400> SEQUENCE: 3
aagtgtgatg tttaaatc                                                        18

<210> SEQ ID NO 4
<211> LENGTH: 18
<212> TYPE: DNA
<213> ORGANISM: Artificial Sequence
<220> FEATURE:
<223> OTHER INFORMATION: Synthetic DNA

<400> SEQUENCE: 4
gacaagaatg cctctgtc                                                        18

<210> SEQ ID NO 5
<211> LENGTH: 18
<212> TYPE: DNA
<213> ORGANISM: Artificial Sequence
<220> FEATURE:
<223> OTHER INFORMATION: Synthetic DNA

<400> SEQUENCE: 5
gcctgttgaa atcgcaat                                                        18

<210> SEQ ID NO 6
```

```
<211> LENGTH: 18
<212> TYPE: DNA
<213> ORGANISM: Artificial Sequence
<220> FEATURE:
<223> OTHER INFORMATION: Synthetic DNA

<400> SEQUENCE: 6
agcgattgaa atttatcc                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetic DNA

<400> SEQUENCE: 7
ggtgaccttc atcgtgct                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic DNA

<400> SEQUENCE: 8
taggctatca attaaatg                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetic DNA

<400> SEQUENCE: 9
agttgctatc ggttatcg                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic DNA

<400> SEQUENCE: 10
agttgctatc ggttatcg                                                 18

<210> SEQ ID NO 11
<211> LENGTH: 18
<212> TYPE: DNA
<213> ORGANISM: Artificial Sequence
<220> FEATURE:
<223> OTHER INFORMATION: Synthetic DNA

<400> SEQUENCE: 11 aggttttta tcatcctt                                                  18

<210> SEQ ID NO 12
<211> LENGTH: 18
<212> TYPE: DNA
<213> ORGANISM: Artificial Sequence
<220> FEATURE:
<223> OTHER INFORMATION: Synthetic DNA

<400> SEQUENCE: 12
```

```
gttatatgtt atttgttg                                               18

<210> SEQ ID NO 13
<211> LENGTH: 18
<212> TYPE: DNA
<213> ORGANISM: Artificial Sequence
<220> FEATURE:
<223> OTHER INFORMATION: Synthetic DNA

<400> SEQUENCE: 13
ggcgtaaagg gcgcgcag                                               18

<210> SEQ ID NO 14
<211> LENGTH: 18
<212> TYPE: DNA
<213> ORGANISM: Artificial Sequence
<220> FEATURE:
<223> OTHER INFORMATION: Synthetic DNA

<400> SEQUENCE: 14
acgggacgaa cggcaagg                                               18

<210> SEQ ID NO 15
<211> LENGTH: 18
<212> TYPE: DNA
<213> ORGANISM: Artificial Sequence
<220> FEATURE:
<223> OTHER INFORMATION: Synthetic DNA

<400> SEQUENCE: 15
acatctgttc caaaatct                                               18

<210> SEQ ID NO 16
<211> LENGTH: 18
<212> TYPE: DNA
<213> ORGANISM: Artificial Sequence
<220> FEATURE:
<223> OTHER INFORMATION: Synthetic DNA

<400> SEQUENCE: 16
acttgttggg gatactta                                               18

<210> SEQ ID NO 17
<211> LENGTH: 18
<212> TYPE: DNA
<213> ORGANISM: Artificial Sequence
<220> FEATURE:
<223> OTHER INFORMATION: Synthetic DNA

<400> SEQUENCE: 17
acttccattc caaatctt                                               18

<210> SEQ ID NO 18
<211> LENGTH: 18
<212> TYPE: DNA
<213> ORGANISM: Artificial Sequence
<220> FEATURE:
<223> OTHER INFORMATION: Synthetic DNA

<400> SEQUENCE: 18
tgaattcttt gttagaaa                                               18

<210> SEQ ID NO 19
<211> LENGTH: 18
<212> TYPE: DNA
```

```
<213> ORGANISM: Artificial Sequence
<220> FEATURE:
<223> OTHER INFORMATION: Synthetic DNA

<400> SEQUENCE: 19
gaagtaaaac tgtattac                                                        18

<210> SEQ ID NO 20
<211> LENGTH: 18
<212> TYPE: DNA
<213> ORGANISM: Artificial Sequence
<220> FEATURE:
<223> OTHER INFORMATION: Synthetic DNA

<400> SEQUENCE: 20
ggcaacggtg gcttagtg                                                        18

<210> SEQ ID NO 21
<211> LENGTH: 18
<212> TYPE: DNA
<213> ORGANISM: Artificial Sequence
<220> FEATURE:
<223> OTHER INFORMATION: Synthetic DNA

<400> SEQUENCE: 21
gtataaacga gacacact                                                        18

<210> SEQ ID NO 22
<211> LENGTH: 18
<212> TYPE: DNA
<213> ORGANISM: Artificial Sequence
<220> FEATURE:
<223> OTHER INFORMATION: Synthetic DNA

<400> SEQUENCE: 22
gaaacagata cgacgtgg                                                        18

<210> SEQ ID NO 23
<211> LENGTH: 18
<212> TYPE: DNA
<213> ORGANISM: Artificial Sequence
<220> FEATURE:
<223> OTHER INFORMATION: Synthetic DNA

<400> SEQUENCE: 23
gtgaactccg tattgaag                                                        18

<210> SEQ ID NO 24
<211> LENGTH: 18
<212> TYPE: DNA
<213> ORGANISM: Artificial Sequence
<220> FEATURE:
<223> OTHER INFORMATION: Synthetic DNA

<400> SEQUENCE: 24
tttgatgatc ctgacata                                                        18

<210> SEQ ID NO 25
<211> LENGTH: 18
<212> TYPE: DNA
<213> ORGANISM: Artificial Sequence
<220> FEATURE:
<223> OTHER INFORMATION: Synthetic DNA

<400> SEQUENCE: 25
gtggagtttt aactcatt                                                        18
```

<210> SEQ ID NO 26
<211> LENGTH: 18
<212> TYPE: DNA
<213> ORGANISM: Artificial Sequence
<220> FEATURE:
<223> OTHER INFORMATION: Synthetic DNA

<400> SEQUENCE: 26
aaactgatgg cgattatg                                                     18

<210> SEQ ID NO 27
<211> LENGTH: 18
<212> TYPE: DNA
<213> ORGANISM: Artificial Sequence
<220> FEATURE:
<223> OTHER INFORMATION: Synthetic DNA

<400> SEQUENCE: 27
ccaccacaac ttcagatt                                                     18

<210> SEQ ID NO 28
<211> LENGTH: 18
<212> TYPE: DNA
<213> ORGANISM: Artificial Sequence
<220> FEATURE:
<223> OTHER INFORMATION: Synthetic DNA

<400> SEQUENCE: 28
ttcagggacg cttggcgg                                                     18

<210> SEQ ID NO 29
<211> LENGTH: 18
<212> TYPE: DNA
<213> ORGANISM: Artificial Sequence
<220> FEATURE:
<223> OTHER INFORMATION: Synthetic DNA

<400> SEQUENCE: 29
gtcgaactga tggtggcc                                                     18

<210> SEQ ID NO 30
<211> LENGTH: 18
<212> TYPE: DNA
<213> ORGANISM: Artificial Sequence
<220> FEATURE:
<223> OTHER INFORMATION: Synthetic DNA

<400> SEQUENCE: 30
agatggaaca ccaacact                                                     18

<210> SEQ ID NO 31
<211> LENGTH: 18
<212> TYPE: DNA
<213> ORGANISM: Artificial Sequence
<220> FEATURE:
<223> OTHER INFORMATION: Synthetic DNA

<400> SEQUENCE: 31
gtgatacatg gtaagaaa                                                     18

<210> SEQ ID NO 32
<211> LENGTH: 18
<212> TYPE: DNA
<213> ORGANISM: Artificial Sequence
<220> FEATURE:

```
<223> OTHER INFORMATION: Synthetic DNA

<400> SEQUENCE: 32
gctgctgaat cagtcgaa                                                 18

<210> SEQ ID NO 33
<211> LENGTH: 18
<212> TYPE: DNA
<213> ORGANISM: Artificial Sequence
<220> FEATURE:
<223> OTHER INFORMATION: Synthetic DNA

<400> SEQUENCE: 33
acaggaggtc agtgtctg                                                 18

<210> SEQ ID NO 34
<211> LENGTH: 18
<212> TYPE: DNA
<213> ORGANISM: Artificial Sequence
<220> FEATURE:
<223> OTHER INFORMATION: Synthetic DNA

<400> SEQUENCE: 34
cgggatagcg tcttgttg                                                 18
```

NUCLEIC ACID EXTRACTION AND AMPLIFICATION CONTROLS AND METHODS OF USE THEREOF

CROSS-REFERENCE TO RELATED APPLICATIONS

This application claims the benefit under 35 U.S.C. § 119(e) of U.S. Provisional Application Nos. 62/380,253, filed Aug. 26, 2016 and 62/380,291, filed Aug. 26, 2016. The entire contents of the aforementioned applications are incorporated by reference herein.

FIELD

This disclosure generally relates to the field of molecular biology and genetic analysis, specifically to nucleic acid reagents and to corresponding methods of using the same for monitoring and evaluating nucleic acid extraction and amplification reactions.

BACKGROUND

Extracting a nucleic acid from a cell or tissue sample is an important process in wide variety of research, applied, and clinical settings. The biopharmaceutical industry, for example, uses nucleic acid extraction for the production of drugs, vaccines, and other biologics, as well as when testing for the bioburden in biopharmaceutical manufacturing. In clinical settings, it is necessary to extract nucleic acids from cells and tissue samples to provide, for example, diagnostic, prognostic, and treatment monitoring. Nucleic acid amplification is also a widely used and an important process in many research, applied, and clinical settings.

There is a need for compositions and methods for assessing and monitoring the performance of nucleic acid extraction and amplification reactions.

SUMMARY

Provided herein are methods, compositions, and kits for amplifying a plurality of nucleic acid target sequences in a sample containing a control nucleic acid molecule, the method comprising: performing a plurality of amplification reactions in parallel, each of the plurality of amplification reactions including a portion of the sample and a pair of amplification primers configured to amplify a corresponding target sequence in the control nucleic acid molecule, wherein the control nucleic acid molecule comprises a plurality of different target sequences; forming a plurality of different amplification products corresponding to at least two different target sequences in the control nucleic acid molecule; and determining the presence of at least two different amplification products in the amplification reactions.

In another aspect, provided herein are methods, compositions, and kits for amplifying a plurality of nucleic acid target sequences comprising: distributing both a control nucleic acid molecule and a test nucleic acid sample into a plurality of reaction volumes, where the control nucleic acid molecule includes a plurality of different target sequences and the test nucleic acid sample includes one or more test nucleic acid molecules; subjecting the reaction volumes to nucleic acid amplification conditions and amplifying at least two different target sequences of the control nucleic acid molecule in the reaction volumes using pairs of amplification primers, each pair of amplification primers being used to amplify a different target sequence in the control nucleic acid molecule; and detecting the presence of at least two different amplified target sequences in the reaction volumes.

In another aspect, provided herein are methods, compositions, and kits for amplifying a plurality of nucleic acid target sequences in a sample containing a control nucleic acid molecule, the method comprising: distributing the sample into a plurality of reaction volumes, where the control nucleic acid molecule contains a plurality of different target sequences, and wherein the reaction volumes include at least two different pair of amplification primers configured to amplify a corresponding target sequence in the control nucleic acid molecule; performing amplification reactions in the reaction volumes and forming a plurality of different amplification products corresponding to at least two different target sequences in the control nucleic acid molecule; and determining the presence of at least two different amplification products in the amplification reactions.

In another aspect, provided herein are methods, compositions, and kits for evaluating a plurality of amplification reactions, the method comprising: distributing portions of a nucleic acid sample to individual reaction chambers situated within or upon a support, wherein the nucleic acid sample contains a control nucleic acid molecule and the control nucleic acid molecule contains a plurality of different target sequences; performing a plurality of parallel amplification reactions and forming a plurality of different target amplification products corresponding to at least two different target sequences in the control nucleic acid molecule in the individual reaction chambers, wherein each amplification reaction contains a pair of amplification primers configured to amplify a corresponding target sequence present within the control nucleic acid molecule and at least two of the amplification reactions contain amplification primers configured to amplify different corresponding target sequences present within the control nucleic acid molecule; and quantifying at least two different target amplification products formed in at least two of the individual reaction chambers.

In another aspect, provided herein are nucleic acid constructs comprising a plurality of different amplification target sequences, wherein the amplification target sequences comprise at least a 20 nucleotide portion of a gene selected from Table 3 or its corresponding cDNA. In some embodiments, provided herein are cells or other compositions comprising such nucleic acid constructs.

In another aspect, provided herein are nucleic acid constructs comprising a plurality of different amplification target sequences, wherein the amplification target sequences comprise a sequence selected from the group consisting of SEQ ID NOs: 1-34, or the complement thereof. In some embodiments, provided herein are cells or other compositions comprising such nucleic acid constructs.

In another aspect, provided herein are arrays for nucleic acid amplification, comprising: a support containing a plurality of reaction sites located within the support or upon the support; each of the plurality of reaction sites containing: (i) a control nucleic acid molecule comprising a plurality of different target sequences, (ii) an amplification primer pair configured to amplify a corresponding target sequence, and (ii) a detectably labeled probe configured to hybridize to a nucleic acid sequence generated by extension of at least one of the amplification primers of the pair.

In another aspect, provided herein are methods, compositions, and kits for confirming the efficacy of a nucleic acid extraction procedure using a control sample comprising host cells, such as yeast cells, transformed with a plasmid containing a control nucleic acid molecule comprising a plurality of different target sequences. In some embodiments, the methods provided herein comprise extracting a nucleic acid sample from the transformed host cells using a nucleic acid extraction procedure; and performing amplification on the extracted nucleic acid sample from the host cells using primers directed to at least one of the plurality of different target sequences of the control nucleic acid molecule to confirm nucleic acid extraction from the control sample. In some embodiments, the methods further comprise extracting a nucleic acid sample from a test sample using the same nucleic acid extraction procedure used for nucleic acid extraction from the control sample; and performing amplification on the extracted nucleic acid from the test sample using the same primers directed to the target sequence(s) tested in the control sample to confirm comparable nucleic acid extraction from the test sample.

In another aspect, provided herein are methods, compositions, and kits for confirming nucleic acid extraction from a control sample comprising host cells, such as yeast cells, transformed with a plasmid containing a control nucleic acid molecule comprising a plurality of different target sequences. In some embodiments, the methods comprise extracting a nucleic acid sample from the control sample; performing amplification on the extracted nucleic acid sample from the control sample; determining if at least one of the plurality of different target sequences of the control nucleic acid molecule is present in the nucleic acid sample extracted from the control sample thereby confirming nucleic acid extraction from the control sample. In some embodiments, the methods further comprise extracting a nucleic acid sample from a test sample using the same nucleic acid extraction procedure used for nucleic acid extraction from the control sample; and performing amplification on the extracted nucleic acid from the test sample using the same primers directed to the target sequence(s) tested in the control sample to confirm comparable nucleic acid extraction from the test sample.

In another aspect, provide herein are control nucleic acid molecules used to evaluate nucleic acid extraction efficiency from a cell, the control nucleic acid molecule comprising a plurality of different target sequences, wherein the plurality of different target sequences are derived from at least two different microorganisms or genes selected from Table 3 and/or wherein the plurality of different target sequences each comprise a different sequence selected from Table 2 (SEQ ID NOs: 1-34) or the complement thereof.

In another aspect, provided herein are extraction control samples used to evaluate nucleic acid extraction from a test sample, the extraction control samples comprising a collection of host cells, such as yeast cells, transformed with a plasmid containing a control nucleic acid molecule comprising a plurality of different target sequences. In some embodiments the plurality of different target sequences are derived from at least two different microorganisms or genes selected from Table 3 and/or at least two of the plurality of sequences each comprise a different sequence selected from Table 2 (SEQ ID NOs: 1-34) or the complement thereof.

In another aspect, provided herein are methods, compositions, and kits for performing amplification on a nucleic acid sample derived from a cell sample containing cells transformed with a plasmid comprising a control nucleic acid molecule, wherein the control nucleic acid molecule comprises a plurality of different target sequences derived from different genomic or transcriptomic regions. In some embodiments, the methods comprise obtaining a derivative nucleic acid sample by deriving nucleic acid molecules from a cell sample containing cells transformed with a plasmid containing a control nucleic acid molecule, wherein the control nucleic acid molecule contains a plurality of different target sequences derived from different genomic or transcriptomic regions; and subjecting the derived nucleic acid sample to amplification conditions sufficient for generating one or more amplification products derived from the control nucleic acid molecule, wherein at least one of the amplification products contain one of the target sequences. In some embodiments, the methods further comprise obtaining additional derived nucleic acid samples by deriving nucleic acid molecules from test samples, wherein the test samples are derived from biological organisms and do not contain the control nucleic acid molecule, and subjecting the additional derived nucleic acid samples to amplification conditions sufficient for generating one or more amplification products containing a target nucleic acid sequence that is identical or complementary to a target sequence of the control nucleic acid molecule.

In another aspect, provided herein are methods, compositions, and kits for performing nucleic acid extraction comprising: obtaining a cell preparation comprising yeast cells transformed with a control nucleic acid molecule, wherein the control nucleic acid molecule contains a plurality of different target sequences derived from different genes of a microorganism or a panel of microorganisms; and extracting a nucleic acid sample from the cell preparation.

These and other features of the present teachings are provided herein.

BRIEF DESCRIPTION OF THE DRAWINGS

The skilled artisan will understand that the drawings described below, are for illustration purposes only. The drawings are not intended to limit the scope of the present teachings in any way.

DESCRIPTION OF EXEMPLARY EMBODIMENTS

Figures 1A, 1B:
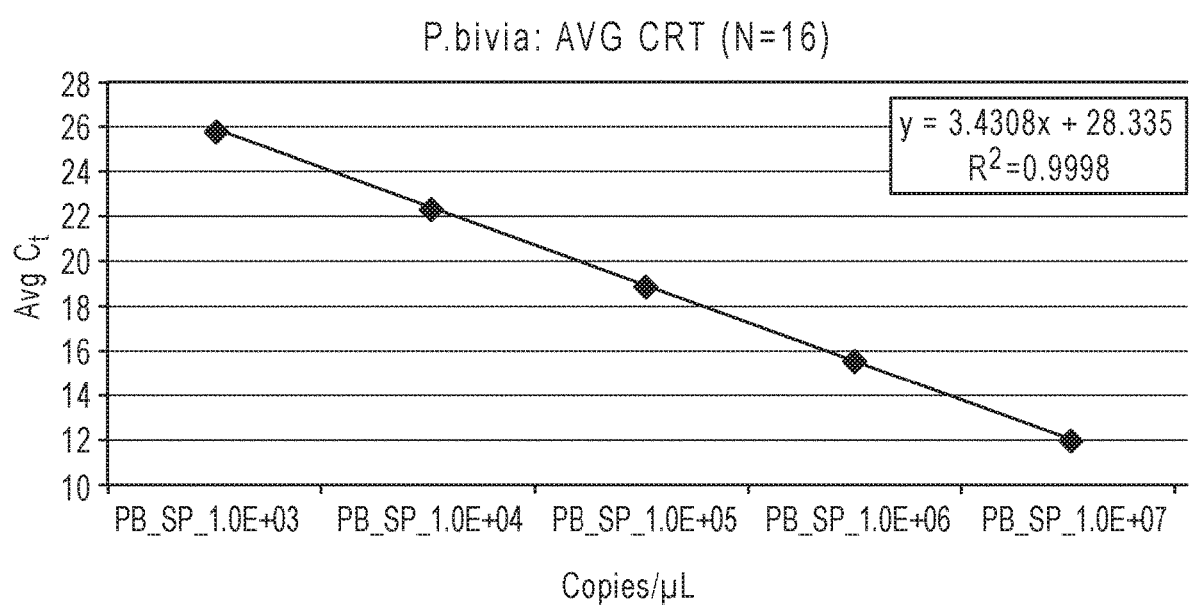
FIG. 1A, FIG. 1B and FIG. 1C depict graphical results for the limit of detection and linear dynamic range, amplification curves, and average Ct values for *Prevotella bivia* TaqMan assay (see Table 3) using linearized control superplasmid DNA as the nucleic acid sample, as provided herein. Nucleic acid samples were provided at varying concentrations, as indicated ($1 \times 10^3$ to $1 \times 10^7$).

In some embodiments, the disclosure relates generally to compositions for use as extraction and/or amplification controls and to methods for the use thereof in nucleic acid extraction and/or nucleic acid amplification processes. The provided control compositions and methods for their use provide users thereof tools and methods to monitor, evaluate, troubleshoot, and control nucleic acid extraction and/or amplification workflows. Whether it is used as part of an extraction control and/or as an amplification control, the control nucleic acid molecules provided herein comprise a plurality of different target sequences.

The provided extraction and/or amplification control nucleic acid compositions can serve as positive and/or negative controls for workflows involving nucleic acid extraction and/or nucleic acid amplification and/or detection. In some embodiments, the control compositions and methods for the use thereof provided herein may be used in conjunction with compositions and methods for amplification and characterization of select nucleic acids, or their respective cDNAs, derived from microorganisms in a biological sample. The control compositions and methods for use thereof as provided herein may be used in conjunction with compositions and methods for the detection of and/or evaluating microbiota profiles of select tissues and anatomical regions, for example, for detecting and/or monitoring vaginal, respiratory and urogenital microbiome constituents and dynamics. As such, when used in conjunction with extraction processes and/or amplification reactions for a select set of assays for target nucleic acids or microorganisms in a biological sample, the control nucleic acid molecules used include the same target sequences to which the amplification and/or detection assays are directed. In some embodiments, the control nucleic acid molecules include a subset of the target sequences to which the assays are directed. In some embodiments, the control nucleic acid molecules include additional target sequences to which additional reference or control assays are directed. In some embodiments, the control nucleic acid molecules include xeno target sequences (with no known homology to any organism) to which control assays are directed.

In some embodiments, the disclosure relates generally to a method for extracting nucleic acid from a cell including a control nucleic acid molecule containing a plurality of different target sequences. In some embodiments, the extracted nucleic acid is detected and/or evaluated via a plurality of amplification reactions performed in parallel as described herein. In some embodiments, the control nucleic acid molecule is in a cell. In certain embodiments, the control nucleic acid molecule is in a microbial cell, including without limitation, a yeast cell. Accordingly, in some embodiments, provided herein are cells comprising a control nucleic acid molecule, the control nucleic acid molecule containing a plurality of different target sequences. In certain embodiments, provided herein are microbial cells comprising a control nucleic acid molecule, the control nucleic acid molecule containing a plurality of different target sequences.

In some embodiments, provided herein are yeast cells comprising a control nucleic acid molecule, the control nucleic acid molecule containing a plurality of different target sequences, the target sequences being derived from a microbial gene, or its cDNA.

In some embodiments, the disclosure relates generally to methods for amplifying a plurality of target sequences in a control nucleic acid molecule sample including contacting at least some portion of the sample with a plurality of target-specific primers as disclosed herein and a polymerase under amplification conditions thereby producing at least one amplified target sequence. As described herein, the control nucleic acid molecule contains a plurality of different target nucleic acid sequences. In some embodiments, the disclosure provides methods for amplifying a plurality of target sequences in a control nucleic acid molecule sample including contacting at least some portion of the sample with a plurality of target-specific primers as disclosed herein and a polymerase under amplification conditions thereby producing at least one amplified target sequence, wherein each of the target-specific primers is provided in a multiplicity of separate reactions (e.g., as single-plex reactions). In some embodiments, the disclosure provides methods for amplifying a plurality of target sequences in a control nucleic acid molecule sample including contacting at least some portion of the sample with a plurality of target-specific primers as disclosed herein and a polymerase under amplification conditions thereby producing at least one amplified target sequence, wherein the plurality of target-specific primers are provided in a single, combined reaction (e.g., as a multiplex reaction). In some embodiments, the methods provided herein comprise contacting at least some portion of the sample with a plurality of target-specific primer and probe sets (e.g., assays) as disclosed herein and a polymerase under amplification conditions thereby producing at least one amplified target sequence and detecting the presence of the at least one amplified target sequence. In some embodiments, each assay includes a forward primer and a reverse primer designed to specifically amplify a target sequence and a detectably labeled probe specific for the nucleic acid amplified by the forward and reverse primers (e.g., an amplicon).

In some embodiments, the methods provided herein include subjecting a sample comprising a control nucleic acid molecule comprising a plurality of different target sequences to multiple individual amplification reactions (i.e. single-plex reactions), each individual reaction performed with a pair of amplification primers designed to be specific for at least a portion of a target sequence in the control nucleic acid molecule and a detectably labeled probe specific of the target sequence amplified by the primers. The multiple individual amplification reactions can generate individual amplification products in separate reactions for each of the target sequences for which the amplification primers and detector probe are designed. Evaluation of the multiple amplification reactions can be arrived at by determining the presence or absence of, and/or by quantifying, the targeted amplification products from the individual (single-plex) amplification reactions.

In some embodiments, the methods provided herein include subjecting a sample comprising a control nucleic acid molecule containing a plurality of different target sequences to an amplification reaction comprising a combination of primer pairs designed to be specific for a plurality of target sequences in the control nucleic acid sample (i.e. multiplex reaction). In some embodiments, the reaction is performed with at least two different pairs of amplification primers designed to be specific for at least two different target sequences in the control nucleic acid molecule and a detectably labeled probe specific for each of the different target sequences amplified by the different primers. In some embodiments, the amplification reaction can generate multiple amplification products for each of the target sequences for which the combination of amplification primers and detector probes are designed. Evaluation of the multiple amplification reactions can be arrived at by determining the presence or absence of, and/or by quantifying, the targeted amplification products within the combined (multiplex) amplification reaction.

In some embodiments, detection assays of the compositions and methods provided herein involve the use of oligonucleotide primers and a detectably labeled probe for amplification and detection of control nucleic acid specific target sequences. In some embodiments, the target-specific primer and probe sets are provided as part of a single-plex reaction. In other embodiments, the target specific primer and probe sets are provided as part of a multiplex reaction.

In some embodiments, detection assays of the compositions and methods provided herein involve the use of oligonucleotide primers and a detectable nucleic acid binding moiety for amplification and detection of control nucleic acid specific target sequences. In some embodiments, the target-specific primer and the detectable nucleic acid binding moiety are provided as part of a single-plex reaction. In other embodiments, the target specific primer and the detectable nucleic acid binding moiety are provided as part of a multiplex reaction. In some embodiments, the detectable nucleic acid binding moiety is a nucleic acid binding dye. In some embodiments, the dye is a double-stranded DNA binding dye. In some embodiments, the dye is SYBR Green.

In some embodiments, the compositions, methods and kits provided herein include additional amplification reactions and assays which are performed as additional reference or control reactions and assays. Without limitation, these additional reference or control reactions and assays can be used in relative quantification applications to assess the adequacy of the biological sample or the nucleic acid sample, to normalize microbial presence, and/or to detect the presence of amplification inhibitors in the biological or nucleic acid sample. Exemplary target nucleic acids for such additional reference or control assays include, without limitation, prokaryotic 16S rRNA gene sequence, human RNase P gene sequence, xeno nucleic acid (XNA) sequence and/or added exogenous nucleic acids.

In some embodiments, the disclosure relates generally to compositions, methods, and kits for performing a plurality of single-plex nucleic acid amplification reactions under the same assay conditions and/or at substantially the same time. In some embodiments, the disclosure relates to compositions, methods, and kits for performing multiplex nucleic acid amplification reactions under the same assay conditions and/or at substantially the same time.

In some embodiments, this disclosure relates generally to compositions, methods, and kits for detecting, monitoring, and evaluating extraction and/or amplification of control nucleic acid molecules containing certain sets of target sequences derived from certain target microorganisms. In some embodiments, the control nucleic acid molecule is part of a plasmid comprising multiple target sequences (i.e., a multi-target plasmid or superplasmid). For example, in some embodiments as described herein, an amplification and/or extraction control nucleic acid molecule was developed to contain at least two different target sequences derived from the microorganisms listed in Table 1 and/or the microorgan-ism genes listed in Table 3. In other embodiments, an amplification and/or extraction control nucleic acid molecule was developed to contain at least two different target sequences comprising a sequence listed in Table 2. In some embodiments, compositions and methods are provided for detection of target sequences derived from at least one of the microorganisms listed in Table 1 and/or the microorganism genes listed in Table 3. In some embodiments, compositions and methods are provided for detection of target sequences comprising a sequence listed in Table 2. In some embodiments, compositions and methods are provided for detection of at least two different target sequences derived from at least two of the microorganisms listed in Table 1 and/or at least two of the microorganism genes listed in Table 3. In some embodiments, compositions and methods are provided for detection of at least two different target sequences comprising a sequence listed in Table 2. In some embodiments, compositions and methods are provided for detection of different target sequences derived from a select group or panel of the microorganisms listed in Table 1 and/or the microorganism genes listed in Table 3. In some embodiments, compositions and methods are provided for detection of different target sequences comprising a select group or panel of the sequences listed in Table 2. In some embodiments, compositions and methods are provided for detection of different target sequences derived from all of the microorganisms listed in Table 1 and/or the microorganism genes listed in Table 3. In some embodiments, compositions and methods are provided for detection of different target sequences each comprising one of the sequences listed in Table 2.

An Applied Biosystems™ TaqMan™ Assay is a combination of an amplification primer pair (forward primer and reverse primer) and a fluorescently labeled probe designed to work in combination to amplify and detect a particular target nucleic acid. In some embodiments, the compositions and methods disclosed herein include microorganism-specific and/or gene-specific TaqMan assays. In some embodiments, the compositions and methods disclosed herein include microorganism-specific TaqMan assays directed to vaginal, urogenital, and/or respiratory microbiota. In some embodiments, the compositions and methods disclosed herein include at least one of the primer pairs and probes provided in the Applied Biosystems™ TaqMan™ Assays listed in Table 3. In some embodiments, methods include at least two different sets of primer pairs and probes provided in the TaqMan™ Assays listed in Table 3. In some embodiments, methods include a select group or panel of the different sets of primer pairs and probes provided in the TaqMan™ Assays listed in Table 3. In some embodiments, methods include all of the different sets of primer pairs and probes provided in the TaqMan™ Assays listed in Table 3.

TABLE 1

| Microorganisms | |
|---|---|
| Microorganism Type | Microorganism name |
| Bacteria | *Atopobium vaginae* |
| Bacteria | *Bacteroides fragilis* |
| Bacteria | BVAB2 |
| Bacteria | *Chlamydia/Chlamydia trachomatis* |
| Bacteria | *Enterococcus faecalis* |
| Bacteria | *Escherichia coli* |
| Bacteria | *Gardnerella vaginalis* |
| Bacteria | Chancroid/*Haemophilus ducreyi* |
| Bacteria | *Lactobacillus crispatus* |
| Bacteria | *Lactobacillus gasseri* |

TABLE 1-continued

| Microorganism Type | Microorganism name |
|---|---|
| Bacteria | *Lactobacillus iners* |
| Bacteria | *Lactobacillus jensenii* |
| Bacteria | Megasphera 1 |
| Bacteria | Megasphera 2 |
| Bacteria | *Mobiluncus curtisii* |
| Bacteria | *Mobiluncus mulieris* |
| Bacteria | *Mycoplasma genitalium* |
| Bacteria | *Mycoplasma hominis* |
| Bacteria | Gonorrhea/*Neisseria gonorrhoeae* |
| Bacteria | *Prevotella bivia* |
| Bacteria | *Staphylococcus aureus* |
| Bacteria | *Streptococcus agalactiae* (Group B Step) |
| Bacteria | *Treponema pallidum* (Syphilis) |
| Bacteria | *Ureaplasma urealyticum* |
| Fungi | *Candida albicans* |
| Fungi | *Candida dubliniensis* |
| Fungi | *Candida glabrata* |
| Fungi | *Candida krusei* |
| Fungi | *Candida lusitaniae* |
| Fungi | *Candida parapsilosis* |
| Fungi | *Candida tropicalis* |
| Protozoa | *Trichomonas/Trichomonas vaginalis* |
| Virus | Herpes simplex virus 1 (HSV1) |
| Virus | Herpes simplex virus 2 (HSV2) |

TABLE 2

Microorganisms and Amplicon-associated Sequences

| Microorganism name | Amplicon-associated Sequence | SEQ ID NO. |
|---|---|---|
| *Atopobium vaginae* | GAGCGTGTAACTGTTAAA | 1 |
| *Bacteroides fragilis* | TTTGCATAATGAATCTGA | 2 |
| BVAB2 | AAGTGTGATGTTTAAATC | 3 |
| *Chlamydia trachomatis* | GACAAGAATGCCTCTGTC | 4 |
| *Enterococcus faecalis* | GCCTGTTGAAATCGCAAT | 5 |
| *Escherichia coli* | AGCGATTGAAATTTATCC | 6 |
| *Gardnerella vaginalis* | GGTGACCTTCATCGTGCT | 7 |
| *Haemophilus ducreyi* | TAGGCTATCAATTAAATG | 8 |
| *Lactobacillus crispatus* | AGTTGCTATCGGTTATCG | 9 |
| *Lactobacillus gasseri* | AGTTGCTATCGGTTATCG | 10 |
| *Lactobacillus iners* | AGGTTTTTTATCATCCTT | 11 |
| *Lactobacillus jensenii* | GTTATATGTTATTTGTTG | 12 |
| Megasphera 1 | GGCGTAAAGGGCGCGCAG | 13 |
| Megasphera 2 | ACGGGACGAACGGCAAGG | 14 |
| *Mobiluncus curtisii* | ACATCTGTTCCAAAATCT | 15 |
| *Mobiluncus mulieris* | ACTTGTTGGGGATACTTA | 16 |
| *Mycoplasma genitalium* | ACTTCCATTCCAAATCTT | 17 |
| *Mycoplasma hominis* | TGAATTCTTTGTTAGAAA | 18 |
| *Neisseria gonorrhoeae* | GAAGTAAAACTGTATTAC | 19 |
| *Prevotella bivia* | GGCAACGGTGGCTTAGTG | 20 |
| *Staphylococcus aureus* | GTATAAACGAGACACACT | 21 |
| *Streptococcus agalactiae* (group B) | GAAACAGATACGACGTGG | 22 |
| *Treponema pallidum* (Syphilis) | GTGAACTCCGTATTGAAG | 23 |
| *Ureaplasma urealyticum* | TTTGATGATCCTGACATA | 24 |
| *Candida albicans* | GTGGAGTTTTAACTCATT | 25 |
| *Candida dubliniensis* | AAACTGATGGCGATTATG | 26 |

TABLE 2-continued

Microorganisms and Amplicon-associated Sequences

| Microorganism name | Amplicon-associated Sequence | SEQ ID NO. |
|---|---|---|
| Candida glabrata | CCACCACAACTTCAGATT | 27 |
| Candida krusei | TTCAGGGACGCTTGGCGG | 28 |
| Candida lusitaniae | GTCGAACTGATGGTGGCC | 29 |
| Candida parapsilosis | AGATGGAACACCAACACT | 30 |
| Candida tropicalis | GTGATACATGGTAAGAAA | 31 |
| Trichomonas vaginalis | GCTGCTGAATCAGTCGAA | 32 |
| HSV1 | ACAGGAGGTCAGTGTCTG | 33 |
| HSV2 | CGGGATAGCGTCTTGTTG | 34 |

TABLE 3

Microorganisms, Genes and Assay Numbers

| Microorganism name | Gene name | TaqMan Assay ID Number |
|---|---|---|
| Atopobium vaginae | 50S ribosomal protein L3 | Ba04646222_s1 |
| Bacteroides fragilis | DNA polymerase sliding clamp subunit | Ba04646225_s1 |
| BVAB2 | 16S ribosomal RNA | Ba04646229_s1 |
| Chlamydia/Chlamydia trachomatis | translocated actin-recruiting phosphoprotein | Ba04646249_s1 |
| Enterococcus faecalis | Aminotransferase claim V | Ba04646247_s1 |
| Escherichia coli | Zinc (II) responsive transcriptional activator, MerR family | Ba04646242_s1 |
| Gardnerella vaginalis | beta subunit of RNA polymerase | Ba04646236_s1 |
| Chancroid/Haemophilus ducreyi | hemoglobin receptor | Ba04646228_s1 |
| Lactobacillus crispatus | carbamoyl-phosphate synthase large subunit | Ba04646245_s1 |
| Lactobacillus gasseri | LaCOG01543 (Predicted transcriptional regulator) | Ba04646234_s1 |
| Lactobacillus iners | HMPREF0520_RS00305 | Ba04646257_s1 |
| Lactobacillus jensenii | guanine permease | Ba04646258_s1 |
| Megasphera 1 | 16S ribosomal RNA | Ba04646230_s1 |
| Megasphera 2 | 16S ribosomal RNA | Ba04646231_s1 |
| Mobiluncus curtisii | tetR family transcriptional regulator | Ba04646235_s1 |
| Mobiluncus mulieris | response regulator containing a CheY-like receiver domain and an HTH DNA-binding domain | Ba04646246_s1 |
| Mycoplasma genitalium | MG192 = mgpC | Ba04646251_s1 |
| Mycoplasma hominis | MHO_RS00005 | Ba04646255_s1 |
| Gonorrheaa/Neisseria gonorrhoeae | NGO0357 | Ba04646252_s1 |
| Prevotella bivia | peptidyl-prolyl cys-trans isomerase | Ba04646278_s1 |
| Staphylococcus aureus | ribonuclease P RNA | Ba04646259_s1 |
| Streptococcus agalactiae (Group B Strep) | surface interaction protein | Ba04646276_s1 |
| Treponema pallidum (Syphilis) | DNA-directed DNA polymerase I | Ba04646237_s1 |
| Ureaplasma urealyticum | UreB | Ba04646254_s1 |
| Candida albicans | inositol phosphoryl transferase | Fn04646233_s1 |
| Candida dubliniensis | tubulin 1 | Fn04646244_s1 |
| Candida glabrata | tubulin 4 | Fn04646240_s1 |
| Candida krusei | 18S ribosomal RNA | Fn04646250_s1 |
| Candida lusitaniae | SKN7 | Fn04646241_s1 |
| Candida parapsilosis | tubulin 4 | Fn04646221_s1 |
| Candida tropicalis | tubulin 4 | Fn04646220_s1 |
| Trichomonas/Trichomonas vaginalis | alpha tubulin 1 | Pr04646256_s1 |
| Herpes simplex virus 1 (HSV1) | virion host shutoff protein | Vi04230116_s1 |
| Herpes simplex virus 2 (HSV2) | UL41-UL42 intergenic spacer | Vi04646232_s1 |

In some embodiments, control nucleic acid molecules are provided which contain target sequences derived from selected genomic or transcriptomic sequences of different microorganisms. In some embodiments, target sequences are derived from genomic or transcriptomic sequences from bacteria, fungi, protozoa, and/or viruses. In some embodiments, control nucleic acid molecules are provided which comprise a plurality of different target sequences derived from different genomic or transcriptomic sequences of different microorganisms. In some embodiments, control nucleic acid molecules are provided which comprise from 2 to about 50 different target sequences derived from different microbial genes. In certain embodiments, control nucleic acid molecules are provided which comprise from 5 to 60, from 10 to 50, or from 20 to 40 different target sequences derived from different microbial genes. In some embodiments, control nucleic acid molecules are provided containing at least 5, at least 10, at least 15, at least 20, at least 25, at least 30, at least 35, at least 40, at least 45, or at least 50 different target sequences derived from different microbial genes.

In some embodiments, provided are control nucleic acid molecules which contain different target sequences derived from the microorganisms listed in Table 1. In some embodiments, provided are control nucleic acid molecules which contain different target sequences derived from the microorganism genes listed in Table 3. In some embodiments, provided are control nucleic acid molecules which include different target sequences, each target sequence comprising a different amplicon-associated sequence (SEQ ID NOs: 1-34) listed in Table 2 or the complement thereof. In some embodiments, the control nucleic acid molecule includes 34 different target sequences and each of the different target sequences comprises one of the sequences listed in Table 2 or the complement thereof. In certain embodiments, the provided control nucleic acid molecules comprise at least 2, at least 5, at least 10, at least 15, at least 20, at least 25, or at least 30 different target sequences, each of the different target sequences comprising a sequence selected from the group consisting of SEQ ID NO: 1-34 or the complement thereof. In some embodiments, the provided control nucleic acid molecules comprise from about 5 to about 30, from about 10 to about 30, from about 15 to about 30, or from about 20 to about 30 different target sequences, each of the different target sequences comprising a sequence selected from the group consisting of SEQ ID NO: 1-34 or the complement thereof. In some embodiments, the provided control nucleic acid molecules comprise 10, 11, 12, 13, 14, 15, 16, 17, 18, 19, 20, 21, 22, 23, 24, 25, 26, 27, 28, 29, 30, 31, 32, 33, or 34 different target sequences, each of the different target sequences comprising a sequence selected from the group consisting of SEQ ID NO: 1-34 or the complement thereof. In some embodiments, the control nucleic acid molecule comprises 34 different target sequences where each of the different target sequences comprise a sequence selected from the group of sequences listed in Table 2 or the complement thereof, as well as additional target sequences for general detection of bacterial and/or human DNA. In some embodiments, the additional target sequences can include, but are not limited to, target sequences from prokaryotic 16S rRNA gene and/or human RNase P gene sequences. In some embodiments, the additional target sequences can include xeno nucleic acid (XNA) sequences.

In some embodiments, the different target sequences in the control nucleic acid molecules vary in length. For example, in some embodiments, each of the different target sequences in the control nucleic acid molecule are from about 15 nucleotides to about 1000 nucleotides in length. In some embodiments, each of the different target sequences in the control nucleic acid molecule are from about 20 to about 800, about 25 to about 600, about 30 to about 500, about 40 to about 400, about 50 to about 300 nucleotides in length.

Figure 5:
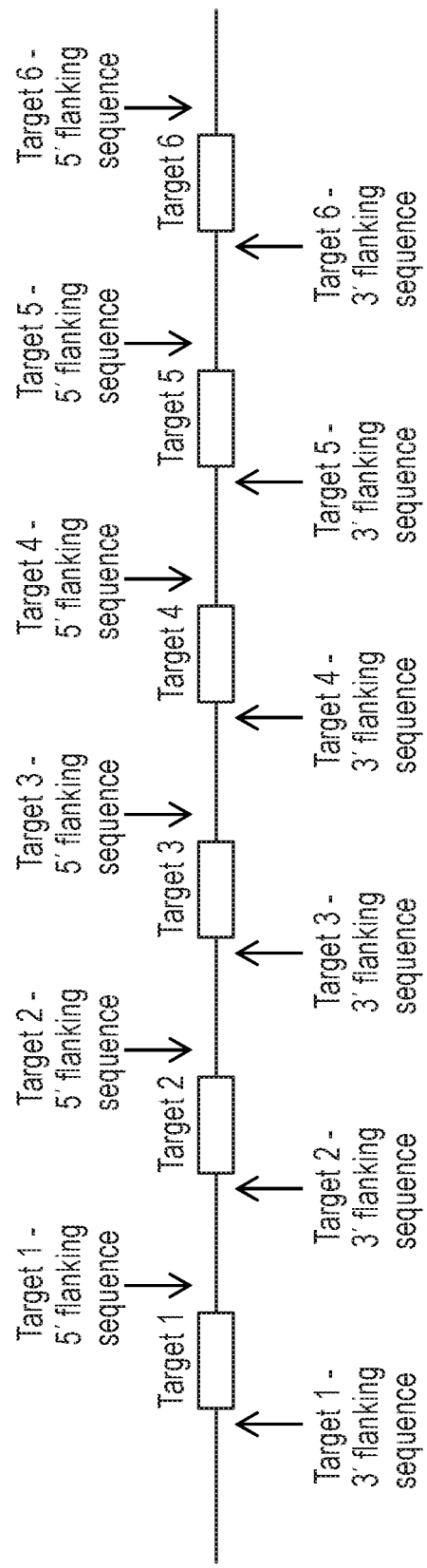
FIG. 5 depicts an illustrative example of one embodiment of a control nucleic acid molecule, as provided herein. In this example, the control nucleic acid sequence includes a plurality of target sequences as well as the corresponding 3' and 5' genomic sequences associated with each target sequence. In other examples (not shown), no flanking sequences are present in the control nucleic acid molecule or only the corresponding 3' or only the corresponding 5' flanking sequence for each target sequence is included in the nucleic acid molecule.

In some embodiments, the control nucleic acid molecule further comprises a portion of the genomic or transcriptomic sequence or sequences which flank either side or both sides of the different target sequences. In some embodiments, the control nucleic acid molecule comprises a portion of the 3' flanking sequence, a portion of the 5' flanking sequence or a portion of both the 3' and 5' flanking sequence for at least two of the different target sequences of the control nucleic acid molecule. In some embodiments, the control nucleic acid molecule comprises a portion of the 3' flanking sequence, a portion of the 5' flanking sequence or a portion of both the 3' and 5' flanking sequence corresponding to each of the different genomic or transcriptomic target sequences of the control nucleic acid molecule (FIG. 5). In some embodiments, the flanking sequence (if 3' or 5') or sequences (if 3' and 5') corresponding to the genomic or transcriptomic region or regions flanking each of the target sequences is between 5 and 500 nucleotides in length. In some embodiments, the flanking sequence(s) corresponding to the genomic or transcriptomic region or regions flanking each of the target sequences is from about 10 to 400, about 15 to 200, about 20 to 100, or about 25 to 50 nucleotides in length. In some embodiments, the control nucleic acid molecule comprises a plurality of target sequences derived from selected genomic or transcriptomic sequences of different microorganisms as well as their corresponding 3', 5', or 3' and 5' genomic or transcriptomic flanking sequences (FIG. 5). In some embodiments, the control nucleic acid molecule comprises flanking sequences corresponding to only a portion of the plurality of different target sequences. For example, flanking sequence can be included in the target nucleic acid molecule for only 1, 2, 3, 4, 5, 6, 10, 15, 20, 25, or 30, etc. of the different target sequences. In some embodiments, the plurality of different target sequences and only their corresponding 3' flanking sequences are included in the control nucleic acid molecule. In some embodiments, the plurality of different target sequences and only their corresponding 5' flanking sequences are included in the control nucleic acid molecule. In some embodiments, the plurality of different target sequences and both their corresponding 3'- and 5'-flanking sequences are included in the control nucleic acid molecule. In some embodiments, the plurality of different target sequences and a combination of either the corresponding 3' flanking, 5' flanking, 3' and 5' flanking or no flanking sequences for each target sequence are in the control nucleic acid molecule. In some embodiments, the control nucleic acid molecule does not comprise any corresponding genomic or transcriptomic flanking sequences.

As described herein, the control nucleic acid molecule comprising the different target sequences (with or without flanking sequences included) can vary in length. In some embodiments, the length of the entire control nucleic acid molecule is between 0.5 kb to 50 kb in length. In some embodiments, the entire control nucleic acid molecule is from about 1 kb to 20 kb, about 2 kb to 15 kb, about 3 kb to 10 kb in length, or about 4 kb to 5 kb in length. In some embodiments a portion of or the entire sequence of the control nucleic acid molecule is inserted into or contained within a nucleic acid construct including, without limitation, a vector, plasmid, or virus.

In some embodiments, provided are methods for assessing nucleic acid amplification which include performing a plurality of amplification reactions in parallel with the control nucleic acid molecule and panels of amplification primer pairs and corresponding detectably labeled probes, wherein each primer/probe combination is specific for a different target sequence of the control nucleic acid molecule. In some embodiments, provided are panels of amplification primer pairs specific for the portions of microbial gene target sequences of the control nucleic acid molecule. In some embodiments, provided are panels of amplification primer pairs and corresponding detectably labeled probes, where each primer/probe combination is specific for a microbial gene target sequence of the control nucleic acid molecule. In some embodiments, provided are panels of amplification primer pairs specific for the portions of microbial gene target sequences of the control nucleic acid molecule and a detectable nucleic acid binding moiety. In some embodiments, the panel of amplification primer pairs includes at least one primer pair for at least one of the microorganisms listed in Table 1 and/or the microbial genes listed in Table 3. In some embodiments, the panel of amplification primer pairs and corresponding detectably labeled probes includes at least one primer/probe combination specific for at least one of the microorganisms listed in Table 1 and/or the microbial genes listed in Table 3. In some embodiments, the panel of amplification primer pairs and corresponding detectably labeled probes includes at least one of the assays listed in Table 2.

In some embodiments, provided are methods for assessing nucleic acid extraction efficiency of a particular method which include extracting a nucleic acid sample from a control sample of cells transformed with a construct comprising the control nucleic acid molecule, performing amplification on the extracted nucleic acid sample from the control sample and determining if at least one of the plurality of different target sequences of the control nucleic acid is present in the extracted nucleic acid sample from the control sample. In some embodiments, the transformed cells are transformed microbial cells. In some embodiments, the transformed cells are transformed yeast cells. In some embodiments, the transformed cells are provided as a lyophilized pellet.

When applying quantitative methods to polymerase chain reaction (PCR)-based technologies, a fluorescent probe or other detectable label may be incorporated into the reaction to provide a means for determining the progress of the target amplification. In some embodiments, through the use of the fluorescent probe or other detectable label, such as a nucleic acid binding moiety, the reaction can be made to fluoresce in relative proportion to the quantity of nucleic acid product produced. As such, when using PCR, assays for nucleotide sequences corresponding to the control target sequences can be used to determine the efficacy of the amplification reaction and/or extraction process for the control nucleic acid sample. In some embodiments, the fluorescent probe can be used in a sequence-specific manner for detection of specific nucleic acids. In some embodiments, the detectable label can be used in a non-sequence-specific manner for general detection of nucleic acids.

In some embodiments, the amplification reactions occur on a support having a plurality of reaction sites and each reaction site contains one pair of amplification primers. In some embodiments, the amplification reactions occur in reaction vessels and each reaction contains one pair of amplification primers. In some embodiments, the reaction vessel further contains at least one target specific oligonucleotide probe, the probe being specific for a portion of the nucleic acid amplified by the amplification primer pair present in the reaction vessel. In certain embodiments, the reaction vessels are through-holes in a support plate and each through-hole contains one pair of amplification primers and at least one detectably-labeled probe as described herein. In some embodiments, the primers or primers and probes are dried in each reaction site or reaction vessel prior to addition of the control nucleic acid sample.

The amplification reaction vessel can also contain other component reagents of the amplification reaction mixture such as, for example, dNTPs (dATP, dCTP, dGTP and/or dTTP), polymerase, buffer(s), salt(s), detergent(s), amplification inhibitor blocking agent(s), and/or antifoam agent(s). Accordingly, in some embodiments, semi-solid or solid supports are provided with reaction sites or reaction vessels comprising a control nucleic acid molecule and an amplification primer pair together with an amplification reaction mixture or master mix. In some embodiments, the primer pair and reaction mix combination in the reaction site or reaction vessel is dried prior to addition of the control nucleic acid sample. In some embodiments, semi-solid or solid supports are provided with reaction sites or reaction vessels comprising a control nucleic acid molecule, an amplification primer pair and detectably labeled probe together with an amplification reaction mixture or master mix. In some embodiments, the primer pair, probe, and reaction mix combination in the reaction site or reaction vessel is dried prior to addition of the control nucleic acid sample.

In some embodiments, supports are provided comprising a reaction site or reaction vessel containing the control nucleic acid molecule and a primer or a primer pair specific for at least one of the microorganisms listed in Table 1 and/or the microorganism genes listed in Table 3. In some embodiments, supports are provided comprising a reaction site or reaction vessel containing the control nucleic acid molecule and a primer or a primer pair specific for at least one of the microorganisms listed in Table 1 and/or the microorganism genes listed in Table 3. In some embodiments, supports are provided comprising a reaction site or reaction vessel containing the control nucleic acid molecule and at least one of the assays listed in Table 3. In some embodiments, supports are provided comprising a plurality of reaction sites or reaction vessels wherein a reaction site or reaction vessel includes the control nucleic acid molecule and a primer or a primer pair specific for at least two of the microorganisms and a corresponding target sequence comprising one of the sequences listed in Table 2 or the complement thereof. In some embodiments, supports are provided comprising a plurality of reaction sites or reaction vessels where a reaction site or reaction vessel includes the control nucleic acid molecule and a primer or a primer pair specific for all of the microorganisms and for their corresponding target sequence comprising one of the sequences listed in Table 2 or the complement thereof. In some embodiments, supports are provided comprising a plurality of reaction sites or reaction vessels where a reaction site or reaction vessel includes the control nucleic acid molecule and a primer or a primer pair specific for at least 10, 11, 12, 13, 14, 15, 16, 17, 18, 19, 20, 21, 22, 23, 24, 25, 26, 27, 28, 29, 30, 31, 32, or 33 of the microorganisms and corresponding target sequence comprising one of the sequences listed in Table 2 or the complement thereof.

In some embodiments, supports are provided comprising a reaction site or reaction vessel containing the control nucleic acid molecule and a primer or a primer pair and a detectably labeled probe each specific for at least one of the microorganisms listed in Table 1 and/or the microorganism genes listed in Table 3. In some embodiments, supports are provided comprising a reaction site or reaction vessel containing the control nucleic acid molecule and a primer or a primer pair and a detectably labeled probe each specific for at least one of the microorganism genes listed in Table 3. In some embodiments, supports are provided comprising a plurality of reaction sites or reaction vessels where a reaction site or reaction vessel includes the control nucleic acid molecule and a primer or a primer pair and a detectably labeled probe each specific for at least two of the microorganisms and a corresponding target sequence comprising one of the sequences listed in Table 2 or the complement thereof. In some embodiments, supports are provided comprising a plurality of reaction sites or reaction vessels where a reaction site or reaction vessel includes the control nucleic acid molecule and a primer or primer pair and a detectably labeled probe each specific for all of the microorganisms and for their corresponding target sequence comprising one of the sequences listed in Table 2 or the complement thereof. In some embodiments, supports are provided comprising a plurality of reaction sites or reaction vessels where a reaction site or reaction vessel includes the control nucleic acid molecule and a primer or a primer pair and a detectably labeled probe each specific for at least 10, 11, 12, 13, 14, 15, 16, 17, 18, 19, 20, 21, 22, 23, 24, 25, 26, 27, 28, 29, 30, 31, 32, or 33 of the microorganisms and corresponding target sequence comprising one of the sequences listed in Table 2 or the complement thereof.

The control nucleic acid molecule provided herein may be DNA or RNA, and may comprise nucleic acid analogs or other nucleic acid mimics. The control nucleic acid molecule may be a single-stranded or double-stranded nucleic acid molecule and may be in the any nucleic acid structure or shape including, but not limited to, linear, circular, supercoiled, nicked circular. The control nucleic acid molecule may be obtained from any source, and may comprise any number of different compositional components. The control nucleic acid may be synthesized by methods known in the art. The control nucleic acid may be synthesized and amplified in vitro or may be transformed or transfected into a cell and amplified within the cell. For example, the control nucleic acid may be inserted into or contained within a nucleic acid construct including, without limitation, a vector, plasmid, or virus, which capable of replication in host cells such as, for example, bacteria, yeast, and eukaryotic cells. In some embodiments, the control nucleic acid molecule is provided in the form of a plasmid. In some embodiments, the control nucleic acid may be within a nucleic acid vector that is capable of replicating in more than one cell type or carrying the control nucleic acid from one cell type to another cell type. In some embodiments, the control nucleic acid molecule is provided in the form of a yeast shuttle vector.

In some embodiments, the control nucleic acid molecule may be obtained from any number of biological sources, including without limitation, viruses, prokaryotes and eukaryotes, for example, from a bacterial culture, from a yeast cell culture, or from a eukaryotic cell line. It will be appreciated that control nucleic acid molecules may be isolated from a biological source using any of a variety of procedures known in the art, for example, MagMAX™ DNA Multi-Sample Ultra Kit (Applied Biosystems, Thermo Fisher Scientific), the MagMAX™ Express-96 Magnetic Particle Processor and the KingFisher™ Flex Magnetic Particle Processor (Thermo Fisher Scientific), the ABI Prism™ 6100 Nucleic Acid PrepStation and the ABI Prism™ 6700 Automated Nucleic Acid Workstation (Applied Biosystems, Thermo Fisher Scientific), and the like. It will be appreciated that control nucleic acids may be linearized prior to analysis, including the use of such procedures as mechanical force, restriction endonuclease cleavage, or any method known in the art. In some embodiments, the control nucleic acids may be in a crude lysate when amplified and/or analyzed.

In some embodiments, an extraction control nucleic acid or a cell composition comprising an extraction control nucleic acid is provided. In some embodiments, the extraction control nucleic acid molecule can be used to detect, monitor and/or evaluate extraction and/or purification of nucleic acids from a cell or other source. The extraction control nucleic acid control undergoes the process of nucleic acid extraction. For example, the extraction control may be within a cell prior to the extraction process. In some embodiments, the extraction control is a microbial cell, for example as a yeast cell, comprising a control nucleic acid molecule. In some embodiments, the extraction control is a prokaryotic cell transformed with a construct, such as a plasmid or shuttle vector, which comprises a control nucleic acid molecule, as provided herein. In other embodiments, the extraction control is a eukaryotic cell comprising a control nucleic acid molecule. In some embodiments, the extraction control is a eukaryotic cell transformed with a construct, such as a plasmid or shuttle vector, which comprises a control nucleic acid molecule, as provided herein. Prior to undergoing lysis and/or a nucleic acid extraction process, the cell preparation containing the control nucleic acid molecule may be in any form including, but not limited to, lyophilized, frozen, embedded in a medium, or in a liquid or viscous medium.

In some embodiments, detection, monitoring, and/or evaluation of the nucleic acid extraction process is assessed through amplification of one or more of the plurality of different target sequences of the extraction control nucleic acid molecule. The assessment amplification and detection of the extraction control nucleic acid molecule can be performed via the methods described herein for the amplification and detection of the amplification control nucleic acid molecule.

To more clearly and concisely describe and point out the subject matter of the present disclosure, the following definitions are provided for specific terms, which are used in the following description and the appended claims. Throughout the specification, exemplification of specific terms should be considered as non-limiting examples.

As used in this specification, the words "a" or "an" means at least one, unless specifically stated otherwise. In this specification, the use of the singular includes the plural unless specifically stated otherwise. For example, but not as a limitation, "a target nucleic acid" means that more than one target nucleic acid can be present; for example, one or more copies of a particular target nucleic acid species, as well as two or more different species of target nucleic acid. The term "and/or" means that the terms before and after the slash can be taken together or separately. For illustration purposes, but not as a limitation, "X and/or Y" can mean "X" or "Y" or "X" and "Y".

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in this specification, embodiments in this specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

As used herein, the terms "amplification", "nucleic acid amplification", or "amplifying" refer to the production of multiple copies of a nucleic acid template, or the production of multiple nucleic acid sequence copies that are complementary to the nucleic acid template. The terms (including the term "polymerizing") may also refer to extending a nucleic acid template (e.g., by polymerization). The amplification reaction may be a polymerase-mediated extension reaction such as, for example, a polymerase chain reaction (PCR). However, any of the known amplification reactions may be suitable for use as described herein. The term "amplifying" that typically refers to an "exponential" increase in target nucleic acid may be used herein to describe both linear and exponential increases in the numbers of a select target sequence of nucleic acid.

The terms "amplicon" and "amplification product" as used herein generally refer to the product of an amplification reaction. An amplicon may be double-stranded or single-stranded, and may include the separated component strands obtained by denaturing a double-stranded amplification product. In certain embodiments, the amplicon of one amplification cycle can serve as a template in a subsequent amplification cycle.

The terms "annealing" and "hybridizing", including, without limitation, variations of the root words "hybridize" and "anneal", are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers and probes anneal to complementary sequences are well known in the art, e.g., as described in *Nucleic Acid Hybridization, A Practical Approach*, Hames and Higgins, eds., IRL Press, Washington, D.C. (1985) and Wetmur and Davidson, *Mol. Biol.* 31:349 (1968).

In general, whether such annealing takes place is influenced by, among other things, the length of the complementary portions of the complementary portions of the primers and their corresponding binding sites in the target flanking sequences and/or amplicons, or the corresponding complementary portions of a reporter probe and its binding site; the pH; the temperature; the presence of mono- and divalent cations; the proportion of G and C nucleotides in the hybridizing region; the viscosity of the medium; and the presence of denaturants. Such variables influence the time required for hybridization. Thus, the preferred annealing conditions will depend upon the particular application. Such conditions, however, can be routinely determined by persons of ordinary skill in the art, without undue experimentation. Preferably, annealing conditions are selected to allow the primers and/or probes to selectively hybridize with a complementary sequence in the corresponding target flanking sequence or amplicon, but not hybridize to any significant degree to different target nucleic acids or non-target sequences in the reaction composition at the second reaction temperature.

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The terms "denaturing" and "denaturation" as used herein refer to any process in which a double-stranded polynucleotide, including without limitation, a genomic DNA (gDNA) fragment comprising at least one target nucleic acid, a double-stranded amplicon, or a polynucleotide including at least one double-stranded segment is converted to two single-stranded polynucleotides or to a single-stranded or substantially single-stranded polynucleotide, as appropriate. Denaturing a double-stranded polynucleotide includes, without limitation, a variety of thermal and chemical techniques which render a double-stranded nucleic acid single-stranded or substantially single-stranded, for example but not limited to, releasing the two individual single-stranded components of a double-stranded polynucleotide or a duplex comprising two oligonucleotides. Those in the art will appreciate that the denaturing technique employed is generally not limiting unless it substantially interferes with a subsequent annealing or enzymatic step of an amplification reaction, or in certain methods, the detection of a fluorescent signal.

As used herein, the term "Tm" is used in reference to melting temperature. The melting temperature is the temperature at which a population of double-stranded nucleic acid molecules becomes half dissociated into single strands.

The term "minor groove binder" as used herein refers to a small molecule that fits into the minor groove of double-stranded DNA, sometimes in a sequence specific manner. Generally, minor groove binders are long, flat molecules that can adopt a crescent-like shape and thus, fit snugly into the minor groove of a double helix, often displacing water. Minor groove binding molecules typically comprise several aromatic rings connected by bonds with torsional freedom, for example, but not limited to, furan, benzene, or pyrrole rings.

The term "end-point" measurement refers to a method where data collection occurs only once the reaction has been stopped.

The terms "real-time" and "real-time continuous" are interchangeable and refer to a method where data collection occurs through periodic monitoring during the course of the polymerization reaction. Thus, the methods combine amplification and detection into a single step.

As used herein the terms "$C_t$" and "cycle threshold" refer to the time at which fluorescence intensity is greater than background fluorescence. They are characterized by the point in time (or PCR cycle) where the target amplification is first detected. Consequently, the greater the quantity of target DNA in the starting material, the faster a significant increase in fluorescent signal will appear, yielding a lower $C_t$.

As used herein, the term "primer" and its derivatives refer generally to any polynucleotide that can hybridize to a target nucleic acid. In some embodiments, the primer can also serve to prime nucleic acid synthesis. In some embodiments, the primer is a synthetically or biologically produced single-stranded oligonucleotide that is extended by covalent bonding of nucleotide monomers during amplification or polymerization of a nucleic acid molecule. Nucleic acid amplification often is based on nucleic acid synthesis by a nucleic acid polymerase or reverse transcriptase. Many such polymerases or reverse transcriptases require the presence of a primer that may be extended to initiate such nucleic acid synthesis. A primer is typically about 11 bases to about 35 bases in length, although shorter or longer primers may be used depending on the need. In certain embodiments, a primer is 17 bases or longer. In certain embodiments, a primer is about 17 bases to about 25 bases in length. A primer may comprise standard, non-standard, derivatized and modified nucleotides. As will be appreciated by those skilled in the art, the oligonucleotides disclosed herein may be used as one or more primers in various extension, synthesis, or amplification reactions.

Typically, a PCR reaction employs a pair of amplification primers including an "upstream" or "forward" primer and a "downstream" or "reverse" primer, which delimit a region of the RNA or DNA to be amplified. A first primer and a second primer may be either a forward or reverse primer and are used interchangeably herein and are not to be limiting.

The terms "complementarity" and "complementary" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementarity refers to the situation in which each nucleotide unit of one polynucleotide strand or region can hydrogen bond with each nucleotide unit of a second polynucleotide strand or region. "Less than perfect complementarity" refers to the situation in which some, but not all, nucleotide units of two strands or two units can hydrogen bond with each other.

As used herein, the term "reverse complement" refers to a sequence that will anneal/base pair or substantially anneal/base pair to a second oligonucleotide according to the rules defined by Watson-Crick base pairing and the antiparallel nature of the DNA-DNA, RNA-RNA, and RNA-DNA double helices. Thus, as an example, the reverse complement of the RNA sequence 5'-AAUUUGC would be 5'-GCAAAUU. Alternative base pairing schemes, including but not limited to G-U pairing, can also be included in reverse complements.

As used herein, the term "probe" refers to synthetic or biologically produced nucleic acids (DNA or RNA) which, by design or selection, contain specific nucleotide sequences that allow them to hybridize, under defined stringencies, specifically (i.e., preferentially) to target nucleic acid sequences.

In some embodiments, the amplification and/or extraction control nucleic acids provided herein are used in conjunction with amplifying, detecting, profiling and/or monitoring targets in a biological sample.

"Biological sample" or "test sample" includes cells, sections of tissues such as biopsy and autopsy samples, and frozen sections taken for histologic purposes, as well as fluid or secretion specimens that arise from cells or tissues. Such samples include biopsies, blood and blood fractions or products (e.g., serum, platelets, red blood cells, and the like), lymph, bone marrow, sputum, bronchoalveolar lavage, amniotic fluid, hair, skin, cultured cells, e.g., primary cultures, explants, and transformed cells, stool, urine, etc. Prior to target nucleic acid preparation, biological samples may be fresh, frozen or formalin- or paraformalin-fixed paraffin-embedded tissue (FFPE). A "biopsy" refers to the process of removing a tissue sample for diagnostic or prognostic evaluation, and to the tissue specimen itself. The biopsy technique applied will depend on the tissue type to be evaluated (e.g., skin, mucosa, etc.), the size and type of the tissue sample, among other factors. Representative biopsy techniques include, but are not limited to, excisional biopsy, incisional biopsy, needle biopsy, and surgical biopsy For example, in some embodiments, the amplification and/or extraction control nucleic acids provided herein are used in conjunction with amplifying, detecting, profiling and/or monitoring nucleic acids from certain sets of target microorganisms in a biological or test sample. In some embodiments, a biological or test sample is from the vagina (e.g., vaginal mucosa, vaginal area), respiratory tract, and/or urogenital tract and includes cells, tissue and/or fluids (e.g., respiratory secretions, urinary fluids, vaginal secretions and anal secretions) from these anatomical sites.

Samples from the skin, mucosa, or their secretions may be collected using a swab, brush, or scraping tool. Collection systems and media compatible with, for example, respiratory, vaginal or urogenital biological samples are known in the art. Exemplary collection systems and media for such sample types include, but are not limited to, ThinPrep™ Pap test (Hologic Corp.), BD SurePath™ test (Becton, Dickinson and Company), ESwab™ (Copan Diagnostics), Aptima™ Vaginal Swab transport Media (STM) (Hologic), and M4™ MicroTest (Remel), Affirm Ambient Temperature Transport System (Becton, Dickinson and Company), and BD ProbeTec™ Swab diluent Q (Becton, Dickinson and Company).

It will be appreciated that nucleic acids may be isolated from biological samples using any of a variety of procedures known in the art, for example, MagMAX™ DNA Multi-Sample Ultra Kit (Applied Biosystems, Thermo Fisher Scientific), the MagMAX™ Express-96 Magnetic Particle Processor and the KingFisher™ Flex Magnetic Particle Processor (Thermo Fisher Scientific), a RecoverAll™ Total Nucleic Acid Isolation Kit for FFPE and PureLink™ FFPE RNA Isolation Kit (Ambion™, Thermo Fisher Scientific), the ABI Prism™ 6100 Nucleic Acid PrepStation and the ABI Prism™ 6700 Automated Nucleic Acid Workstation (Applied Biosystems, Thermo Fisher Scientific), and the like. It will be appreciated that target nucleic acids from the biological samples may be cut or sheared prior to analysis, including the use of such procedures as mechanical force, sonication, restriction endonuclease cleavage, or any method known in the art.

As used herein, the term "template" is interchangeable with "target molecule" or "target nucleic acid" and refers to a double-stranded or single-stranded nucleic acid molecule which is to be amplified, copied or extended, synthesized, or sequenced. In the case of a double-stranded DNA molecule, denaturation of its strands to form a first and a second strand is performed to amplify, sequence, or synthesize these molecules. Target nucleic acids can include the nucleic acid sequences to which primers useful in the amplification or synthesis reaction can hybridize prior to extension by a polymerase. A primer, complementary to a portion of a template is hybridized under appropriate conditions and the polymerase (e.g., DNA polymerase or reverse transcriptase) may then synthesize a nucleic acid molecule complementary to said template or a portion thereof. The newly synthesized molecule, according to the present disclosure, may be equal or shorter in length than the original template. Mismatch incorporation during the synthesis or extension of the newly synthesized molecule may result in one or a number of mismatched base pairs. Thus, the synthesized molecule need not be exactly complementary to the template. The template may be an RNA molecule, a DNA molecule, or a DNA/RNA hybrid molecule. A newly synthesized molecule may serve as a template for subsequent nucleic acid synthesis or amplification.

The term "incorporating" as used herein, means becoming a part of a DNA or RNA molecule or primer.

The term "nucleic acid binding moiety" as used herein refers to a molecule which has an affinity for binding nucleic acid molecules such as DNA, RNA or DNA/RNA hybrids.

The term "nucleic acid binding dye" as used herein refers to a fluorescent molecule that is specific for a double-stranded polynucleotide or that at least shows a substantially greater fluorescent enhancement when associated with double-stranded polynucleotides than with a single stranded polynucleotide. Typically, nucleic acid binding dye molecules associate with double-stranded segments of polynucleotides by intercalating between the base pairs of the double-stranded segment, but binding in the major or minor grooves of the double-stranded segment, or both. Non-limiting examples of nucleic acid binding dyes include ethidium bromide, DAPI, Hoechst derivatives including without limitation Hoechst 33258 and Hoechst 33342, intercalators comprising a lanthanide chelate (for example, but not limited to, a naphthalene diimide derivative carrying two fluorescent tetradentate β-diketone-$Eu^{3+}$ chelates (NDI-(BHHCT-$Eu^{3+}$)$_2$), see e.g., Nojima et al., *Nucl. Acids Res.* Suppl. No. 1 105 (2001), and certain asymmetrical cyanine dyes such as SYBR® Green and PicoGreen®.

As used herein, the terms "polynucleotide", "oligonucleotide," and "nucleic acid" are used interchangeably and refer to single-stranded and double-stranded polymers of nucleotide monomers, including without limitation, 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $N^+$, and the like. A polynucleotide may be composed entirely of deoxyribonucleotides, entirely of ribonucleotides, or chimeric mixtures thereof and may include nucleotide analogs. The nucleotide monomer units may comprise any of the nucleotides described herein, including, but not limited to, nucleotides and/or nucleotide analogs. Polynucleotides typically range in size from a few monomeric units, e.g., 5-40 when they are sometimes referred to in the art as oligonucleotides, to several thousands of monomeric nucleotide units. Unless denoted otherwise, whenever a polynucleotide sequence is represented, it will be understood that the nucleotides are in the 5'-to-3' order from left to right and that "A" denotes deoxyadenosine, "C" denotes deoxycytosine, "G" denotes deoxyguanosine, "T" denotes deoxythymidine, and "U" denotes deoxyuridine, unless otherwise noted.

The term "nucleotide" refers to a phosphate ester of a nucleoside, e.g., triphosphate esters, wherein the most common site of esterification is the hydroxyl group attached at the C-5 position of the pentose.

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms. When the nucleoside base is purine or 7-deazapurine, the pentose is attached to the nucleobase at the 9-position of the purine or deazapurine, and when the nucleobase is purimidine, the pentose is attached to the nucleobase at the 1-position of the pyrimidine.

The term "analog" includes synthetic analogs having modified base moieties, modified sugar moieties, and/or modified phosphate ester moieties. Phosphate analogs generally comprise analogs of phosphate wherein the phosphorous atom is in the +5 oxidation state and one or more of the oxygen atoms is replaced with a non-oxygen moiety, e.g. sulfur. Exemplary phosphate analogs include: phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4+$, $Na^+$ Exemplary base analogs include: 2,6-diaminopurine, hypoxanthine, pseudouridine, C-5-propyne, isocytosine, isoguanine, 2-thiopyrimidine. Exemplary sugar analogs include: 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, and bromo.

As used herein, the term "superplasmid" refers to a plasmid (DNA molecule) containing an insert fragment that comprises multiple nucleic acid target sequences of interest. In some embodiments, the nucleic acid target sequences can be genomic or transcriptomic sequences. In some embodiments, the nucleic acid target sequences can be xeno nucleic acids (XNA).

As used herein, the term "reaction vessel" generally refers to any container, chamber, device, or assembly, in which a reaction can occur in accordance with the present teachings. In some embodiments, a reaction vessel may be a microtube, for example, but not limited to, a 0.2 mL or a 0.5 mL reaction tube such as a MicroAmp™ Optical tube (Life Technologies Corp., Carlsbad, Calif.) or a micro-centrifuge tube, or other containers of the sort in common practice in molecular biology laboratories. In some embodiments, a reaction vessel comprises a well of a multi-well plate (such as a 48-, 96-, or 384-well microtiter plate), a spot on a glass slide, a well in a TaqMan™ Array Card or a channel or chamber of a microfluidics device, including without limitation a TaqMan™ Low Density Array, or a through-hole of a TaqMan™ OpenArray™ Real-Time PCR plate (Applied Biosystems, Thermo Fisher Scientific). For example, but not as a limitation, a plurality of reaction vessels can reside on the same support. An OpenArray™ Plate, for example, is a reaction plate 3072 through-holes. Each such through-hole in such a plate may contain a single TaqMan™ assay. In some embodiments, lab-on-a-chip-like devices available, for example, from Caliper or Fluidigm can provide reaction vessels. It will be recognized that a variety of reaction vessels are commercially available or can be designed for use in the context of the present teachings.

The term "reporter group" is used in a broad sense herein and refers to any identifiable tag, label, or moiety.

The term "thermostable" when used in reference to an enzyme, refers to an enzyme (such as a polypeptide having nucleic acid polymerase activity) that is resistant to inactivation by heat. A "thermostable" enzyme is in contrast to a "thermolabile" polymerase, which can be inactivated by heat treatment. Thermolabile proteins can be inactivated at physiological temperatures, and can be categorized as meso-thermostable (inactivation at about 45° C. to about 65° C.), and thermostable (inactivation at greater than about 65° C.). For example, the activities of the thermolabile T5 and T7 DNA polymerases can be totally inactivated by exposing the enzymes to a temperature of about 90° C. for about 30 seconds. A thermostable polymerase activity is more resistant to heat inactivation than a thermolabile polymerase. However, a thermostable polymerase does not mean to refer to an enzyme that is totally resistant to heat inactivation; thus heat treatment may reduce the polymerase activity to some extent. A thermostable polymerase typically will also have a higher optimum temperature than thermolabile DNA polymerases.

The term "working concentration" refers to the concentration of a reagent that is at or near the optimal concentration used in a solution to perform a particular function (such as amplification or digestion of a nucleic acid molecule). The working concentration of a reagent is also described equivalently as a "1× concentration" or a "1× solution" (if the reagent is in solution) of the reagent. Accordingly, higher concentrations of the reagent may also be described based on the working concentration; for example, a "2× concentration" or a "2× solution" of a reagent is defined as a concentration or solution that is twice as high as the working concentration of the reagent; a "5× concentration" or a "5× solution" is five times as high as the working concentration, and so on.

The term "amplification reaction mixture" and/or "master mix" may refer to an aqueous solution comprising the various (some or all) reagents used to amplify a target nucleic acid. Such reactions may also be performed using solid supports or semi-solid supports (e.g., an array). The reactions may also be performed in single or multiplex format as desired by the user. These reactions typically include enzymes, aqueous buffers, salts, amplification primers, target nucleic acid, and nucleoside triphosphates. In some embodiments, the amplification reaction mix and/or master mix may include one or more of, for example, a buffer (e.g., Tris), one or more salts (e.g., $MgCl_2$, KCl), glycerol, dNTPs (dA, dT, dG, dC, dU), recombinant BSA (bovine serum albumin), a dye (e.g., ROX passive reference dye), one or more detergents, polyethylene glycol (PEG), polyvinyl pyrrolidone (PVP), gelatin (e.g., fish or bovine source) and/or antifoam agent. Depending upon the context, the mixture can be either a complete or incomplete amplification reaction mixture. In some embodiments, the master mix does not include amplification primers prior to use in an amplification reaction. In some embodiments, the master mix does not include target nucleic acid prior to use in an amplification reaction. In some embodiments, an amplification master mix is mixed with a target nucleic acid sample prior to contact with amplification primers.

In some embodiments, the amplification reaction mixture comprises amplification primers and a master mix. In some embodiments, the amplification reaction mixture comprises amplification primers, a detectably labeled probe, and a master mix. In some embodiments, the reaction mixture of amplification primers and master mix or amplification primers, probe and master mix are dried in a storage vessel or reaction vessel. In some embodiments, the reaction mixture of amplification primers and master mix or amplification primers, probe and master mix are lyophilized in a storage vessel or reaction vessel.

In some embodiments, the disclosure generally relates to the amplification of multiple target-specific sequences from a single control nucleic acid molecule. For example, in some embodiments that single control nucleic acid molecule can include RNA and in other embodiments, that single control nucleic acid molecule can include DNA. In some embodiments, the target-specific primers and primer pairs are target-specific sequences that can amplify specific regions of a nucleic acid molecule, for example, a control nucleic acid molecule. In some embodiments, the target-specific primers can prime reverse transcription of RNA to generate target-specific cDNA. In some embodiments, the target-specific primers can amplify target DNA or cDNA. In some embodiments, the amount of DNA required for selective amplification can be from about 1 ng to 1 microgram. In some embodiments, the amount of DNA required for selective amplification of one or more target sequences can be about 1 ng, about 5 ng or about 10 ng. In some embodiments, the amount of DNA required for selective amplification of target sequence is about 10 ng to about 200 ng.

In one embodiment, a nucleic acid control containing one or more target sequences can be amplified using any one or more of the target-specific primers disclosed herein. In another embodiment, amplified target sequences obtained using the methods and associated compositions and kits disclosed herein, can be coupled to a downstream process, such as but not limited to, nucleic acid sequencing. For example, once the nucleic acid sequence of an amplified target sequence is known, the nucleic acid sequence can be compared to one or more reference samples. The output from the amplification procedure can be optionally analyzed for example by nucleic acid sequencing to determine if the expected amplification product based on the target-specific primers is present in the amplification output. In some embodiments, amplicons generated by the selective amplification can be cloned prior to sequencing or the amplicons can be sequenced directly without cloning. The amplicons can be sequenced using any suitable DNA sequencing platform. In some embodiments, the amplicons can be sequenced using an Ion Personal Genome Machine™ (PGM™) System or an Ion Proton™ System (Thermo Fisher Scientific).

The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR as the nucleic acid amplification reaction, it is expected that the modified detergents describe herein should be effective in other types of nucleic acid amplification reactions, including both polymerase-mediated amplification reactions (such as helicase-dependent amplification (HDA), recombinase-polymerase amplification (RPA), and rolling circle amplification (RCA)), as well as ligase-mediated amplification reactions (such as ligase detection reaction (LDR), ligase chain reaction (LCR), and gap-versions of each), and combinations of nucleic acid amplification reactions such as LDR and PCR (see, for example, U.S. Pat. No. 6,797,470). For example, the modified detergents may be used in, for example, various ligation-mediated reactions, where for example ligation probes are employed as opposed to PCR primers. Additional exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., PCT Pub. No. WO 2006/081222), strand displacement (see, e.g., U.S. Pat. No. RE39007E), partial destruction of primer molecules (see, e.g., PCT Pub. No. WO 2006/087574)), ligase chain reaction (LCR) (see, e.g., Wu, et al., *Genomics* 4: 560-569 (1990)), and/or Barany, et al. *Proc. Natl. Acad. Sci. USA* 88:189-193 (1991)), Qβ RNA replicase systems (see, e.g., PCT Pub. No. WO 1994/016108), RNA transcription-based systems (e.g., TAS, 3SR), rolling circle amplification (RCA) (see, e.g., U.S. Pat. No. 5,854,033; U.S. Pat. Pub. No. 2004/265897; Lizardi et al. *Nat. Genet.* 19: 225-232 (1998); and/or Banér et al. *Nucleic Acid Res.*, 26: 5073-5078 (1998)), and strand displacement amplification (SDA) (Little, et al. *Clin. Chem.* 45:777-784 (1999)), among others. These systems, along with the many other systems available to the skilled artisan, may be suitable for use in polymerizing and/or amplifying target nucleic acids for use as described herein.

In certain embodiments, amplification techniques comprise at least one cycle of amplification, for example, but not limited to, the steps of: denaturing a double-stranded nucleic acid to separate the component strands; hybridizing a primer to a target flanking sequence or a primer-binding site of an amplicon (or complements of either, as appropriate); and synthesizing a strand of nucleotides in a template-dependent manner using a DNA polymerase. The cycle may or may not be repeated. In certain embodiments, a cycle of amplification comprises a multiplicity of amplification cycles, for example, but not limited to 20 cycles, 25 cycles, 30 cycles, 35 cycles, 40 cycles, 45 cycles or more than 45 cycles of amplification.

In some embodiments, amplifying comprises thermal cycling using an instrument, for example, but not limited to, a GeneAmp® PCR System 9700, 9600, 2700 or 2400 thermocycler, an Applied Biosystems® ViiA™ 7 Real-Time PCR System, an Applied Biosystems® 7500 Fast Real-Time PCR System, a 7900HT Fast Real-Time PCR System, a StepOne® Real-Time PCR System, a StepOnePlus® Real-Time PCR System, a QuantStudio™ 12K Flex Real-Time PCR System, a QuantStudio™ Dx Real-Time PCR System and the like (all from Thermo Fisher Scientific). Other examples of spectrophotometric thermal cyclers for use in the methods include, but are not limited to, Bio-Rad ICycler IQ™, Cepheid SmartCycler® II, Corbett Research Rotor-Gene 3000, Idaho Technologies R.A.P.I.D.™ MI Research Chromo 4™, Roche Applied Science LightCycler®, Roche Applied Science LightCycler®2.0, Stratagene Mx3000P™, and Stratagene Mx4000™. In certain embodiments, single-stranded amplicons are generated in an amplification reaction, for example, but not limited to asymmetric PCR or A-PCR.

In some embodiments, one-step RT-PCR is performed in which both the reverse transcription of the target RNA sequence and amplification of the resultant cDNA occurs in the same reaction mixture. In some embodiments, the reaction mixture further includes a detectably labeled, target-specific probe such that detection of the amplified cDNA also occurs in the same reaction mixture.

In certain embodiments, an amplification reaction comprises a plurality or multiplicity of single-plex reactions performed in parallel under the same assay conditions and/or at substantially the same time. In some embodiments, performing the plurality of amplification reactions in parallel forms a plurality of different amplification products. In certain embodiments, performing the plurality of amplification reactions in parallel can form between 10 and 10,000 different amplification products. In some embodiments, performing the plurality of amplification reactions in parallel can form between 10 and 1000 different amplification products. In certain embodiments, performing the plurality of amplification reactions in parallel can form between 10 and 100 different amplification products or between 10 and 50 different amplification products.

In certain embodiments, an amplification reaction comprises multiplex amplification, in which a multiplicity of different target nucleic acids and/or a multiplicity of different amplification product species are simultaneously amplified using a multiplicity of different primer sets. In certain embodiments, a multiplex amplification reaction and a single-plex amplification reaction, including a multiplicity of single-plex or lower-plexy reactions (for example, but not limited to a two-plex, a three-plex, a four-plex, a five-plex or a six-plex reaction) are performed in parallel.

As described herein, exemplary methods for polymerizing and/or amplifying nucleic acids include, for example, polymerase-mediated extension reactions. For instance, the polymerase-mediated extension reaction can be the polymerase chain reaction (PCR). In other embodiments, the nucleic acid amplification reaction is a multiplex reaction. For instance, exemplary methods for polymerizing and/or amplifying and detecting nucleic acids suitable for use as described herein are commercially available as TaqMan® assays (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900, all of which are hereby incorporated herein by reference in their entirety). TaqMan® assays are typically carried out by performing nucleic acid amplification on a target polynucleotide using a nucleic acid polymerase having 5'-to-3' nuclease activity, a primer capable of hybridizing to said target polynucleotide, and an oligonucleotide probe capable of hybridizing to said target polynucleotide 3' relative to said primer. The oligonucleotide probe typically includes a detectable label (e.g., a fluorescent reporter molecule) and a quencher molecule capable of quenching the fluorescence of said reporter molecule. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

In addition to 5'-nuclease probes, such as the probes used in TaqMan® assays, various probes are known in the art and suitable for use in detecting amplified nucleic acids in the provided methods. Exemplary probes include, but are not limited to, various stem-loop molecular beacons (e.g., U.S. Pat. Nos. 6,103,476 and 5,925,517 and Tyagi and Kramer, Nature Biotechnology 14:303-308 (1996)), stemless or linear beacons (e.g., PCT Pub. No. WO 99/21881; U.S. Pat. No. 6,485,901), PNA Molecular Beacons™ (e.g., U.S. Pat. Nos. 6,355,421 and 6,593,091), linear PNA beacons (e.g., Kubista et al., SPIE 4264:53-58 (2001)), non-FRET probes (e.g., U.S. Pat. No. 6,150,097), Sunrise®/Amplifluor® probes (U.S. Pat. No. 6,548,250), stem-loop and duplex Scorpions™ probes (Solinas et al., Nucleic Acids Research 29:E96 (2001) and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes (Svanvik, et al. Anal Biochem 281:26-35 (2000)), self-assembled nanoparticle probes, ferrocene-modified probes described, for example, in U.S. Pat. No. 6,485,901; Mhlanga et al., Methods 25:463-471 (2001); Whitcombe et al., Nature Biotechnology. 17:804-807 (1999); Isacsson et al., Molecular Cell Probes. 14:321-328 (2000); Wolffs et al., Biotechniques 766:769-771 (2001); Tsourkas et al., Nucleic Acids Research. 30:4208-4215 (2002); Riccelli et al., Nucleic Acids Research 30:4088-4093 (2002); Zhang et al., Acta Biochimica et Biophysica Sinica (Shanghai). 34:329-332 (2002); Maxwell et al., J. Am. Chem. Soc. 124:9606-9612 (2002); Broude et al., Trends Biotechnol. 20:249-56 (2002); Huang et al., Chem Res. Toxicol. 15:118-126 (2002); and Yu et al., J. Am. Chem. Soc. 14:11155-11161 (2001); QuantiProbes® (Qiagen), HyBeacons® (French, et al. Mol. Cell. Probes 15:363-374 (2001)), displacement probes (Li, et al. Nucl. Acids Res. 30:e5 (2002)), HybProbes (Cardullo, et al. Proc. Natl. Acad. Sci. USA 85:8790-8794 (1988)), MGB Alert (www.nanogen.com), Q-PNA (Fiandaca, et al. Genome Res. 11:609-611 (2001)), Plexor™ (Promega), LUX™ primers (Nazarenko, et al. Nucleic Acids Res. 30:e37 (2002)), DzyNA primers (Todd, et al. Clin. Chem. 46:625-630 (2000)). Detectably-labeled probes may also comprise non-detectable quencher moieties that quench the fluorescence of the detectable label, including, for example, black hole quenchers (Biosearch), Iowa Black™ quenchers (IDT), QSY quencher (Molecular Probes™; Thermo Fisher Scientific), and Dabsyl and Dabcyl sulfonate/carboxylate Quenchers (Epoch). Detectably-labeled probes may also comprise two probes, wherein for example a fluorophore is on one probe, and a quencher is on the other, wherein hybridization of the two probes together on a target quenches the signal, or wherein hybridization on a target alters the signal signature via a change in fluorescence. Exemplary systems may also include FRET, salicylate/DTPA ligand systems (Oser et al. Angew. Chem. Int.

Engl. 29(10):1167 (1990)), displacement hybridization, homologous probes, and/or assays described in European Pat. No. EP 070685 and/or U.S. Pat. No. 6,238,927. Detectable labels can also comprise sulfonate derivatives of fluorescein dyes with SO3 instead of the carboxylate group, phosphoramidite forms of fluorescein, phosphoramidite forms of Cy5 (available for example from Amersham). All references cited above are hereby incorporated herein by reference in their entirety.

As described herein, one or more detectable labels and/or quenching agents may be attached to one or more primers and/or probes (e.g., detectable label). The detectable label may emit a signal when free or when bound to one of the target nucleic acids. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As described herein, in some embodiments the detectable label may be attached to a probe, which may be incorporated into a primer, or may otherwise bind to amplified target nucleic acid (e.g., a detectable nucleic acid binding agent such as an intercalating or non-intercalating dye). When using more than one detectable label, each should differ in their spectral properties such that the labels may be distinguished from each other, or such that together the detectable labels emit a signal that is not emitted by either detectable label alone. Exemplary detectable labels include, for instance, a fluorescent dye or fluorphore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluoresceins (e.g., 5-carboxy-2,7-dichlorofluorescein; 5-Carboxyfluorescein (5-FAM); 5-Hydroxy Tryptamine (5-HAT); 6-JOE; 6-carboxyfluorescein (6-FAM); FITC; 6-carboxy-1,4-dichloro-2', 7'-dichlorofluorescein (TET); 6-carboxy-1,4-dichloro-2',4', 5',7'-tetrachlorofluorescein (HEX); 6-carboxy-4',5'-dichloro-2',7'-dimethoxy-fluorescein (JOE); Alexa Fluor® fluorophores (e.g., 350, 405, 430, 488, 500, 514, 532, 546, 555, 568, 594, 610, 633, 635, 647, 660, 680, 700, 750); BODIPY™ fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcfluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP. EGFP), blue fluorescent protein (e.g., BFP, EBFP, EBFP2, Azurite, mKalamal), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY@ FL/BODIPY® FL, Fluorescein/QSY7 and QSY9), LysoTracker® and LysoSensor™ (e.g., LysoTracker® Blue DND-22, LysoTracker® Blue-White DPX, LysoTracker® Yellow HCK-123, LysoTracker® Green DND-26, LysoTracker® Red DND-99, LysoSensor™ Blue DND-167, LysoSensor™ Green DND-189, LysoSensor™ Green DND-153, LysoSensor™ Yellow/Blue DND-160, LysoSensor™ Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B can C, Sulphorhodamine G Extra, TAMRA (6-carboxytetramethylrhodamine), Tetramethylrhodamine (TRITC), WT), Texas Red, Texas Red-X, VIC and other labels described in, e.g., U.S. Pat. Pub. No. 2009/0197254 (incorporated herein by reference in its entirety), among others as would be known to those of skill in the art. Other detectable labels may also be used (see, e.g., U.S. Pat. Pub. No. 2009/0197254 (incorporated herein by reference in its entirety)), as would be known to those of skill in the art. Any of these systems and detectable labels, as well as many others, may be used to detect amplified target nucleic acids.

As used herein, the term "detectable label" refers to any of a variety of signaling molecules indicative of amplification. In some embodiments, the reaction mixture may include a detectable label such as SYBR® Green and/or other DNA-binding dyes. Such detectable labels may comprise or may be, for example, nucleic acid intercalating agents or non-intercalating agents. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent may produce a detectable signal directly or indirectly. The signal may be detectable directly using, for example, fluorescence and/or absorbance, or indirectly using, for example, any moiety or ligand that is detectably affected by proximity to double-stranded nucleic As used herein, an intercalating agent is an agent or moiety capable of non-covalent insertion between stacked base pairs of a double-stranded nucleic acid molecule. A non-intercalating agent acid is suitable such as a substituted label moiety or binding ligand attached to the nucleic acid binding agent. It is typically necessary for the nucleic acid binding agent to produce a detectable signal when bound to a double-stranded nucleic acid that is distinguishable from the signal produced when that same agent is in solution or bound to a single-stranded nucleic acid. For example, intercalating agents such as ethidium bromide fluoresce more intensely when intercalated into double-stranded DNA than when bound to single-stranded DNA, RNA, or in solution (e.g., U.S. Pat. Nos. 5,994,056; 6,171, 785; and/or 6,814,934). Similarly, actinomycin D fluoresces in the red portion of the UV/VIS spectrum when bound to single-stranded nucleic acids, and fluoresces in the green portion of the UV/VIS spectrum when bound to double-stranded nucleic acids. And in another example, the photoreactive psoralen 4-aminomethyl-4-5',8-trimethylpsoralen (AMT) has been reported to exhibit decreased absorption at long wavelengths and fluorescence upon intercalation into double-stranded DNA (Johnson et al. Photochem. & Photobiol., 33:785-791 (1981). For example, U.S. Pat. No. 4,257,774 describes the direct binding of fluorescent intercalators to DNA (e.g., ethidium salts, daunomycin, mepacrine and acridine orange, 4',6-diamidino-α-phenylindole). Non-intercalating agents (e.g., minor groove binders as described herein such as Hoechst 33258, distamycin, netropsin) may also be suitable for use. For example, Hoechst 33258 (Searle, et al. Nucl. Acids Res. 18(13):3753-3762 (1990)) exhibits altered fluorescence with an increasing amount of target.

Other DNA binding dyes are available to one of skill in the art and may be used alone or in combination with other agents and/or components of an assay system. Exemplary DNA binding dyes may include, for example, acridines (e.g., acridine orange, acriflavine), actinomycin D (Jain, et al. J. Mol. Biol. 68:21 (1972)), anthramycin, BOBO™-1, BOBO™-3, BO-PRO™-1, cbromomycin, DAPI (Kapuseinski, et al. Nucl. Acids Res. 6(112): 3519 (1979)), daunomycin, distamycin (e.g., distamycin D), dyes described in U.S. Pat. No. 7,387,887, ellipticine, ethidium salts (e.g., ethidium bromide), fluorcoumanin, fluorescent intercalators as described in U.S. Pat. No. 4,257,774, GelStar® (Lonza), Hoechst 33258 (Searle and Embrey, Nucl. Acids Res. 18:3753-3762 (1990)), Hoechst 33342, homidium, JO-PRO™-1, LIZ dyes, LO-PRO™-1, mepacrine, mithramycin, NED dyes, netropsin, 4',6-diamidino-α-phenylindole, proflavine, POPO™-1, POPO™-3, PO-PRO™-1, propidium iodide, ruthenium polypyridyls, S5, SYBR® Gold, SYBR® Green I (U.S. Pat. Nos. 5,436,134 and 5,658,751), SYBR® Green II, SYTOX® blue, SYTOX® green, SYTO® 43, SYTO® 44, SYTO® 45, SYTOX® Blue, TO-PRO®-1, SYTO® 11, SYTO® 13, SYTO® 15, SYTO® 16, SYTO® 20, SYTO® 23, thiazole orange (Sigma-Aldrich Chemical Co.), TOTO™-3, YO-PRO®-1, and YOYO®-3 (Molecular Probes; Thermo Fisher Scientific), among others. SYBR® Green I (e.g., U.S. Pat. Nos. 5,436, 134; 5,658,751; and/or 6,569,927), for example, has been used to monitor a PCR reactions. Other DNA binding dyes may also be suitable as would be understood by one of skill in the art.

Enzymes for use in the methods, compositions and kits provided herein may also include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, et al., Science 239:487-491 (1988); U.S. Pat. Nos. 4,889,818 and 4,965,188), Tne DNA polymerase (WO 96/10640), Tma DNA polymerase (U.S. Pat. No. 5,374,553) and mutants, fragments, variants or derivatives thereof (see, e.g., U.S. Pat. Nos. 5,948,614 and 6,015,668, which are incorporated by reference herein in their entireties). As will be understood by one of ordinary skill in the art, modified reverse transcriptases and DNA polymerase having reverse transcriptase activity may be obtained by recombinant or genetic engineering techniques that are well-known in the art. Mutant reverse transcriptases or polymerases may, for example, be obtained by mutating the gene or genes encoding the reverse transcriptase or polymerase of interest by site-directed or random mutagenesis. Such mutations may include point mutations, deletion mutations and insertional mutations. In some embodiments, one or more point mutations (e.g., substitution of one or more amino acids with one or more different amino acids) are used to construct mutant reverse transcriptases or polymerases for use in the invention. Fragments of reverse transcriptases or polymerases may also be obtained by deletion mutation by recombinant techniques that are well-known in the art, or by enzymatic digestion of the reverse transcriptase(s) or polymerase(s) of interest using any of a number of well-known proteolytic enzymes.

Exemplary polypeptides having reverse transcriptase activity for use in the methods provided herein include Moloney Murine Leukemia Virus (M-MLV) reverse transcriptase, Rous Sarcoma Virus (RSV) reverse transcriptase, Avian Myeloblastosis Virus (AMV) reverse transcriptase, Rous Associated Virus (RAV) reverse transcriptase, Myeloblastosis Associated Virus (MAV) reverse transcriptase and Human Immunodeficiency Virus (HIV) reverse transcriptase, and others described in WO 98/47921 and derivatives, variants, fragments or mutants thereof, and combinations thereof. In a further embodiment, the reverse transcriptases are reduced or substantially reduced in RNase H activity, and may be selected from the group consisting of M-MLV H− reverse transcriptase, RSV H− reverse transcriptase, AMV H-reverse transcriptase, RAV H− reverse transcriptase, MAV H− reverse transcriptase and HIV H− reverse transcriptase, and derivatives, variants, fragments or mutants thereof, and combinations thereof. Reverse transcriptases of particular interest include AMV RT and M-MLV RT, and optionally AMV RT and M-MLV RT having reduced or substantially reduced RNase H activity (e.g., AMV RT alpha H−/BH+ and M-MLV RT H−). Reverse transcriptases for use in the invention include SuperScript™, SuperScript™ II, ThermoScript™ and ThermoScript™ II available from Invitrogen™ (Thermo Fisher Scientific). See generally, WO 98/47921, U.S. Pat. Nos. 5,244,797 and 5,668,005, the entire contents of each of which are herein incorporated by reference.

Polypeptides having reverse transcriptase activity for use in the methods provided herein may be obtained commercially, for example, from Invitrogen™ (Thermo Fisher Scientific), Pharmacia (Piscataway, N.J.), Sigma (Saint Louis, Mo.) or Boehringer Mannheim Biochemicals (Indianapolis, Ind.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, et al., J. Virol. 29:517 (1979)). In addition, the polypeptides having reverse transcriptase activity may be prepared by recombinant DNA techniques that are familiar to one of ordinary skill in the art (see, e.g., Kotewicz, et al., Nucl. Acids Res. 16:265 (1988); Soltis and Skalka, Proc. Natl. Acad. Sci. USA 85:3372-3376 (1988)).

The nucleic acid polymerases that may be employed in the disclosed nucleic acid amplification reactions may be any that function to carry out the desired reaction including, for example, a prokaryotic, fungal, viral, bacteriophage, plant, and/or eukaryotic nucleic acid polymerase. As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'-to-3' direction. Since DNA polymerase can only add a nucleotide onto a pre-existing 3'-OH group, to begin a DNA synthesis reaction, the DNA polymerase needs a primer to which it can add the first nucleotide. Suitable primers may comprise oligonucleotides of RNA or DNA, or chimeras thereof (e.g., RNA/DNA chimerical primers). The DNA polymerases may be a naturally occurring DNA polymerases or a variant of natural enzyme having the above-mentioned activity. For example, it may include a DNA polymerase having a strand displacement activity, a DNA polymerase lacking 5'-to-3' exonuclease activity, a DNA polymerase having a reverse transcriptase activity, or a DNA polymerase having an endonuclease activity.

Polymerases used in accordance with the present teachings may be any enzyme that can synthesize a nucleic acid molecule from a nucleic acid template, typically in the 5' to 3' direction. Suitable nucleic acid polymerases may also comprise holoenzymes, functional portions of the holoenzymes, chimeric polymerase, or any modified polymerase that can effectuate the synthesis of a nucleic acid molecule. Within this disclosure, a DNA polymerase may also include a polymerase, terminal transferase, reverse transcriptase, telomerase, and/or polynucleotide phosphorylase.

The nucleic acid polymerases used in the methods disclosed herein may be mesophilic or thermophilic. Exemplary mesophilic DNA polymerases include T7 DNA polymerase, T5 DNA polymerase, Klenow fragment DNA polymerase, DNA polymerase III and the like. Non-limiting examples of polymerases may include, for example, T7 DNA polymerase, eukaryotic mitochondrial DNA Polymerase γ, prokaryotic DNA polymerase I, II, III, IV, and/or V; eukaryotic polymerase α, β, γ, δ, ε, η, ζ, τ, and/or κ; $E.$ $coli$ DNA polymerase I; $E.$ $coli$ DNA polymerase III alpha and/or epsilon subunits; $E.$ $coli$ polymerase IV, $E.$ $coli$ polymerase V; $T.$ $aquaticus$ DNA polymerase I; $B.$ $stearothermophilus$ DNA polymerase I; Euryarchaeota polymerases; terminal deoxynucleotidyl transferase (TdT); $S.$ $cerevisiae$ polymerase 4; translesion synthesis polymerases; reverse transcriptase; and/or telomerase. Non-limiting examples of suitable thermostable DNA polymerases that may be used include, but are not limited to, $Thermus$ $thermophilus$ (Tth) DNA polymerase, $Thermus$ $aquaticus$ (Taq) DNA polymerase, $Thermotoga$ $neopolitana$ (Tne) DNA polymerase, $Thermotoga$ $maritima$ (Tma) DNA polymerase, $Thermococcus$ $litoralis$ (Tli or VENT™) DNA polymerase, $Pyrococcus$ $furiosus$ (Pfu) DNA polymerase, DEEPVENT™ DNA polymerase, $Pyrococcus$ $woosii$ (Pwo) DNA polymerase, $Bacillus$ $sterothermophilus$ (Bst) DNA polymerase, $Bacillus$ $caldophilus$ (Bca) DNA polymerase, $Sulfobus$ $acidocaldarius$ (Sac) DNA polymerase, $Thermoplasma$ $acidophilum$ (Tac) DNA polymerase, $Thermus$ $flavus$ (Tfl/Tub) DNA polymerase, $Thermus$ $ruber$ (Tru) DNA polymerase, $Thermus$ $brockianus$ (DYNAZYME™) DNA polymerase, $Methanobacterium$ $thermoautotrophicum$ (Mth) DNA polymerase, $mycobacterium$ DNA polymerase (Mtb, Mlep), and mutants, and variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, Gene 112:29-35 (1992); Lawyer, et al., PCR Meth. Appl. 2:275-287 (1993); Flaman, et al., Nucl. Acids Res. 22(15):3259-3260 (1994)). RNA polymerases such as T3, T5 and SP6 and mutants, variants and derivatives thereof may also be used in accordance with the present teachings. Generally, any type I DNA polymerase may be used in accordance with the invention although other DNA polymerases may be used including, but not limited to, type III or family A, B, C etc. DNA polymerases. In addition, any genetically engineered DNA polymerases, any having reduced or insignificant 3'-to-5' exonuclease activity (e.g., SuperScript™ DNA polymerase), and/or genetically engineered DNA polymerases (e.g., those having the active site mutation F667Y or the equivalent of F667Y (e.g., in Tth), AmpliTaq™ FS, ThermoSequenase™), AmpliTaq™ Gold, Platinum™ Taq DNA Polymerase, Therminator I, Therminator II, Therminator III, Therminator Gamma (New England Biolabs, Beverly, Mass.), and/or any derivatives and fragments thereof, may be used in accordance with the present teachings. Examples of DNA polymerases substantially lacking in 3' exonuclease activity include, but are not limited to, Taq, Tne(exo-), Tma(exo-), Pfu (exo-), Pwo(exo-) and Tth DNA polymerases, and mutants, variants and derivatives thereof. Other nucleic acid polymerases may also be suitable as would be understood by one of skill in the art.

DNA polymerases for use in the methods disclosed herein may be obtained commercially, for example, from Invitrogen™ (Thermo Fisher Scientific), Pharmacia (Piscataway, N.J.), Sigma (St. Louis, Mo.), Boehringer Mannheim, and New England Biolabs (Beverly, Mass.).

The detection of the signal may be using any reagents or instruments that detect a change in fluorescence from a fluorophore. For example, detection may be performed using any spectrophotometric thermal cycler. Examples of spectrophotometric thermal cyclers include, but are not limited to, Applied Biosystems (AB) PRISM® 7000, AB 7300 real-time PCR system, AB 7500 real-time PCR system, AB PRISM' 7900HT, Bio-Rad ICycler IQ™, Cepheid SmartCycler® II, Corbett Research Rotor-Gene 3000, Idaho Technologies R.A.P.I.D.™, MJ Research Chromo 4™, Roche Applied Science LightCycler®, Roche Applied Science LightCycler®2.0, Stratagene Mx3000P™, and Stratagene Mx4000™. It should be noted that new instruments are being developed at a rapid rate and any like instruments may be used for the methods.

Kits comprising an amplification and/or extraction control nucleic acid and/or cell composition and kits for performing the methods described herein are also provided. As used herein, the term "kit" refers to a packaged set of related components, typically one or more compounds or compositions. The kit may comprise at least one amplification control nucleic acid composition and may further comprise a pair of oligonucleotides for polymerizing and/or amplifying at least one target sequence from the control nucleic acid, one or more detergents, a nucleic acid polymerase, and/or corresponding one or more probes labeled with a detectable label. The kit may comprise at least one extraction control nucleic acid composition and/or cells containing at least one extraction control nucleic acid molecule, such as in the form of a plasmid, and may further comprise a pair of oligonucleotides for polymerizing and/or amplifying at least one target sequence from the control nucleic acid molecule, one or more detergents, a nucleic acid polymerase, and/or corresponding one or more probes labeled with a detectable label. The kits may also include samples containing other predefined target nucleic acids to be used in control reactions. The kits may also include a pair of oligonucleotides for polymerizing and/or amplifying at least one target nucleic acid from a biological sample. The kits may also optionally include stock solutions, buffers, enzymes, detectable labels or reagents required for detection, tubes, membranes, and the like that may be used to complete the amplification reaction. In some embodiments, multiple primer sets are included. In one embodiment, the kit may include one or more of, for example, a buffer (e.g., Tris), one or more salts (e.g., KCl), glycerol, dNTPs (dA, dT, dG, dC, dU), recombinant BSA (bovine serum albumin), a dye (e.g., ROX passive reference dye), one or more detergents, polyethylene glycol (PEG), polyvinyl pyrrolidone (PVP), gelatin (e.g., fish or bovine source) and/or antifoam agent. Other embodiments of particular systems and kits are also contemplated which would be understood by one of skill in the art.

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

EXAMPLES

A panel of TaqMan™ Assays was designed to detect and/or profile microbiota of vaginal and urogenital samples. A panel of such assays was designed to discriminate between 34 different microorganisms which include both commensural and pathogenic microbes associated with the vagina and the urogenital area. The panel includes assays to detect the bacteria, fungi, protozoa, and viruses as listed in Table 1. To enable those using this assay panel to better control major steps in the workflow, extraction control compositions for sample preparation and amplification control nucleic acids for PCR were designed and developed.

Example 1—Nucleic Acid Amplification Control

For the amplification control nucleic acid molecule, a DNA sequence was designed and the corresponding DNA molecule synthesized to include all the target amplicons and a portion of their flanking regions for the microbe-specific assays in the panel described above, as well as several control templates, including a 100-200 nucleotide xeno sequence and a fragment from the human RNase P gene sequence. A unique restriction site for downstream linearization was also engineered into the DNA sequence comprising the plurality of target amplicons and a portion of each of their corresponding 5'- and 3'-flanking sequences. The synthesized DNA molecule was cloned into a bacterial plasmid vector (pMK from Invitrogen) to create a multitarget plasmid or superplasmid. In this example, the superplasmid was designed to comprise target sequence for the panel of 34 assays listed in Table 3. After transformation of the superplasmid into *E. coli* and subsequent plasmid DNA extraction, the plasmid was linearized at the unique restriction site by restriction enzyme digestion and the plasmid preparation was quantified. The linearized control plasmid preparation was normalized to a final concentration of $1 \times 10^5$ copies/microliter.

Amplification of linearized control plasmid preparations was compared using TaqMan™ OpenArray™ plates (Applied Biosystems) pre-spotted with a panel of 34 different TaqMan™ assays listed in Table 3. Each assay included a pair of amplification primers and an oligonucleotide TaqMan™ probe with a detectable label. The TaqMan™ amplification primers and probe are designed to be target specific for the corresponding genes listed for each assay as shown in Table 3. The amplification reactions were run and analyzed on a QuantStudio™ 12K Flex Real-Time PCR System according to the manufacturer's instructions (Applied Biosystems).

Prior to amplification, the amplification control plasmid preparation was serially diluted across 6 logs from $10^2$ copies per microliter to $10^7$ copies per microliter. For each subarray, a PCR reaction was prepared by adding 2.5 microliters of diluted control plasmid preparation to 2.5 microliters TaqMan™ OpenArray Real-Time PCR Master Mix (Thermo Fisher) according to the manufacturer's instructions. The PCR reaction mix with the control nucleic acid sample at varying concentrations was loaded on the OpenArray™ plates using an OpenArray Accufill System and run on the QuantStudio™ 12K Flex System (Thermo Fisher) per the manufacturer's instructions. In another instance, the amplification control plasmid preparation was also serially diluted across 7 logs from $5 \times 10^7$ copies per microliter to 50 copies per microliter and PCR reactions performed as described.

Figure 1C:
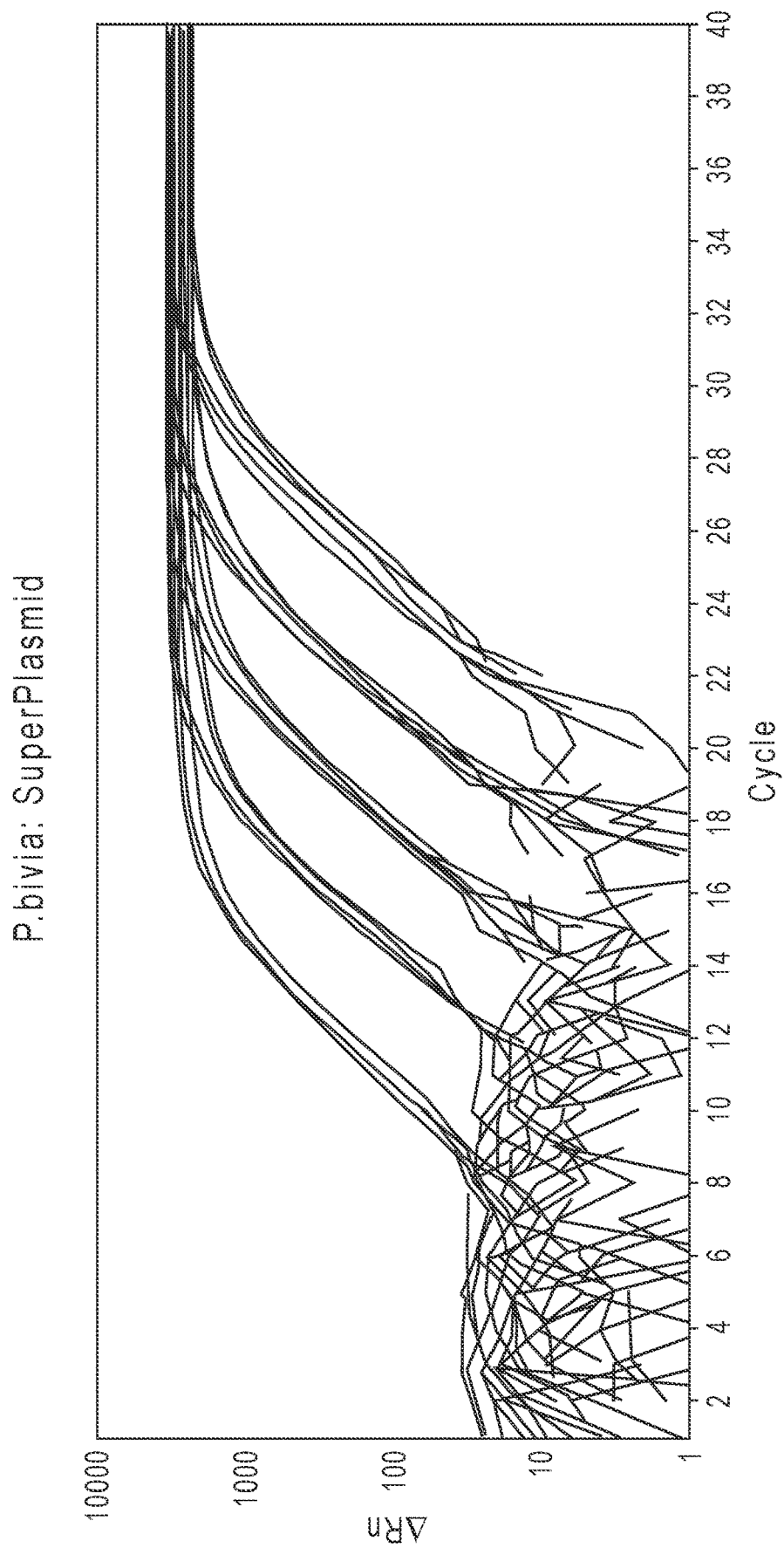
Figure 2A:
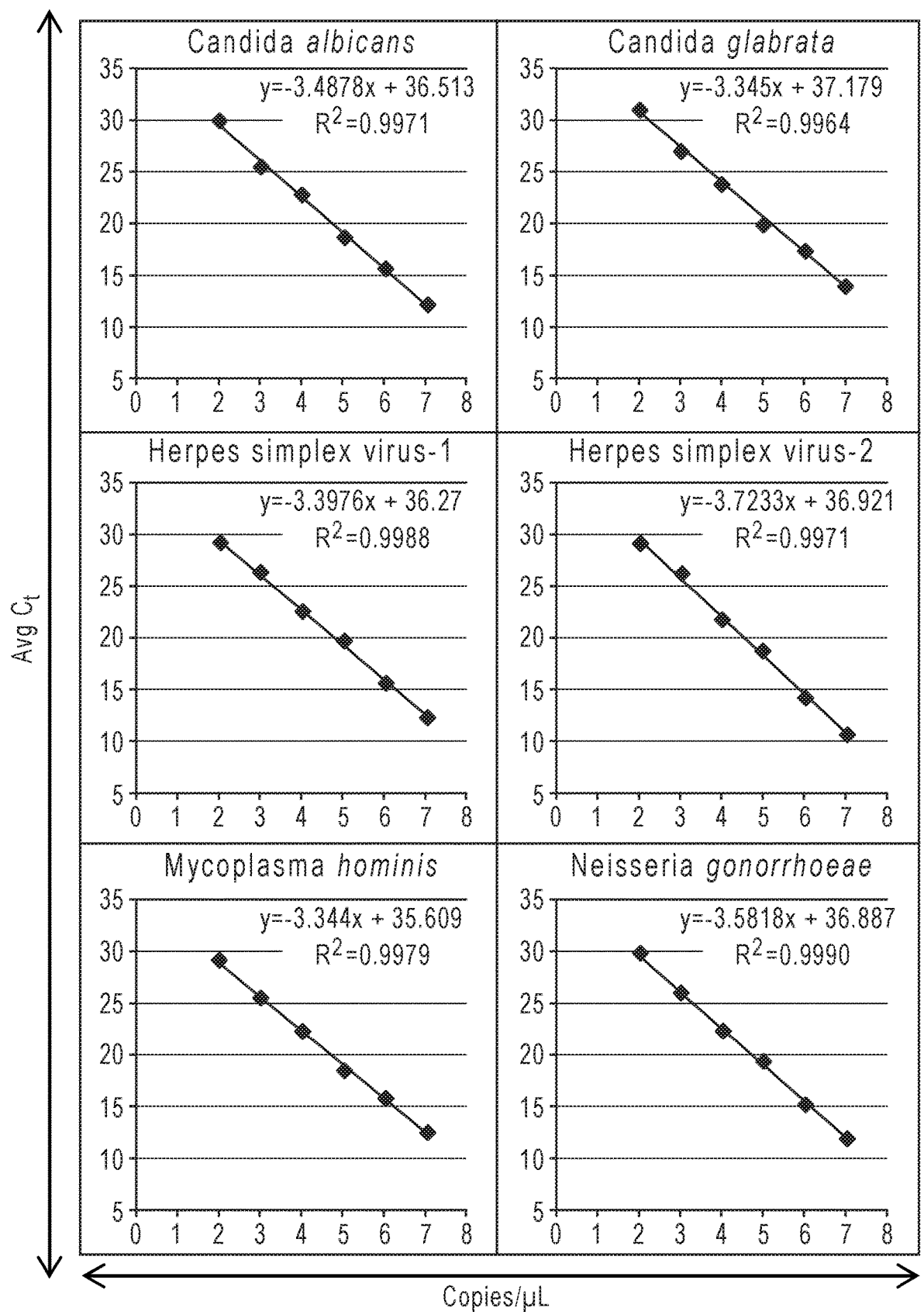
FIG. 2A and FIG. 2B depict graphical results for the limit of detection and linear dynamic range for twelve different exemplary TaqMan assays (see Table 3) using linearized control superplasmid DNA as the nucleic acid sample, as provided herein. Nucleic acid samples were provided at varying concentrations, as indicated ($1 \times 10^2$ to $1 \times 10^7$).
Figure 2B:
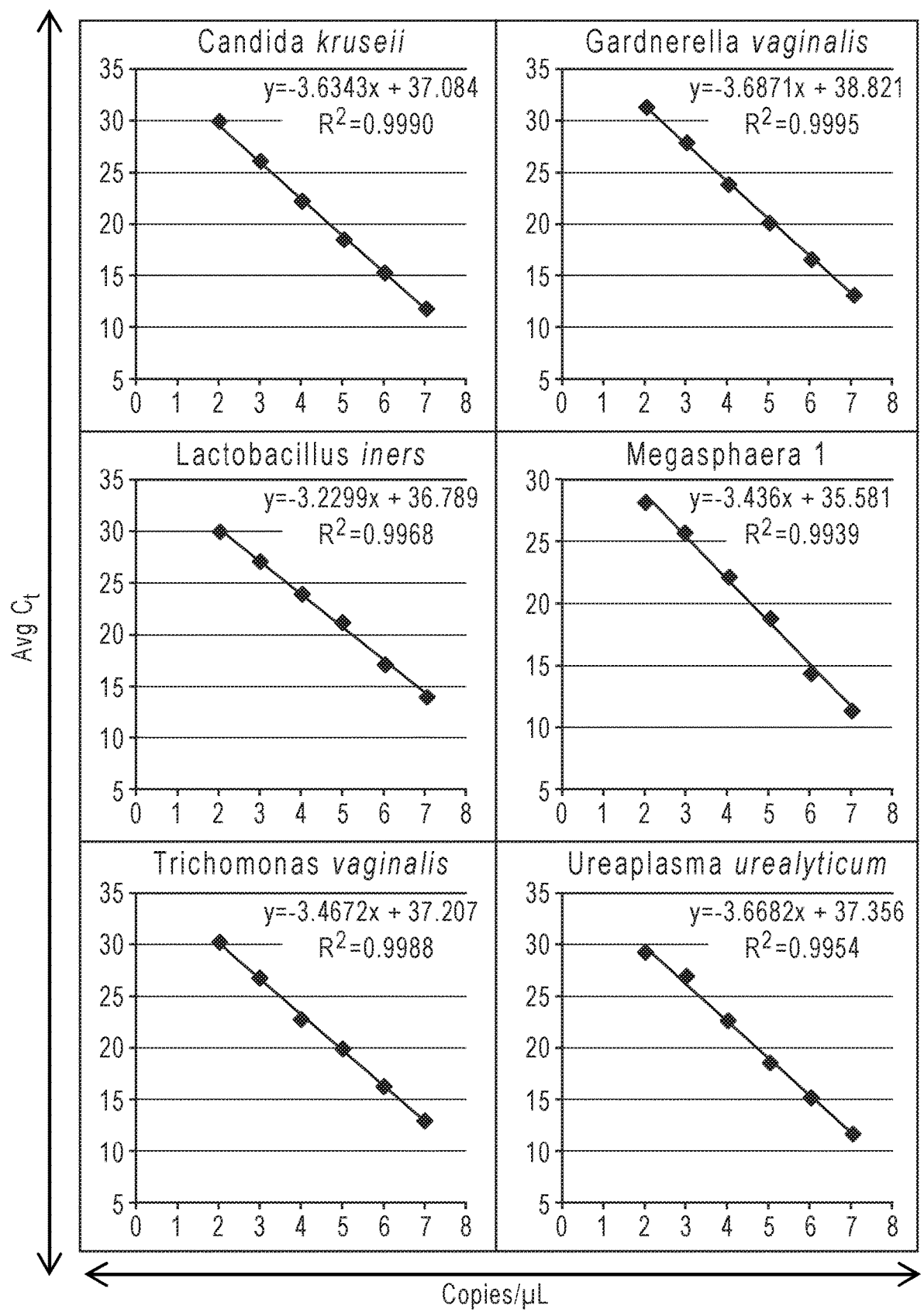

All assays tested showed a limit of detection (LOD) down to about 50-100 copies with 6-7 logs linearity of $R^2$ greater than 0.99. FIGS. 1A-1C depict data from one of the 34 assays tested (*P. bivia* assay) using the linearized control DNA plasmid sample at varying concentrations. FIGS. 2A-2B depict serial dilution data from twelve of the 34 assays tested using the linearized control DNA plasmid sample at varying concentrations. Amplification of the linearized control plasmid was also evaluated using the 34 assay panel by loading nucleic acid samples onto 384 well plates in quadruplicate. Good PCR efficiency and reproducibility were achieved with the linearized control plasmid with each of the different assays tested on both OpenArray (FIGS. 1A-1C and FIGS. 2A-2B) and 384 well plate formats (data not shown).

Figure 3A:
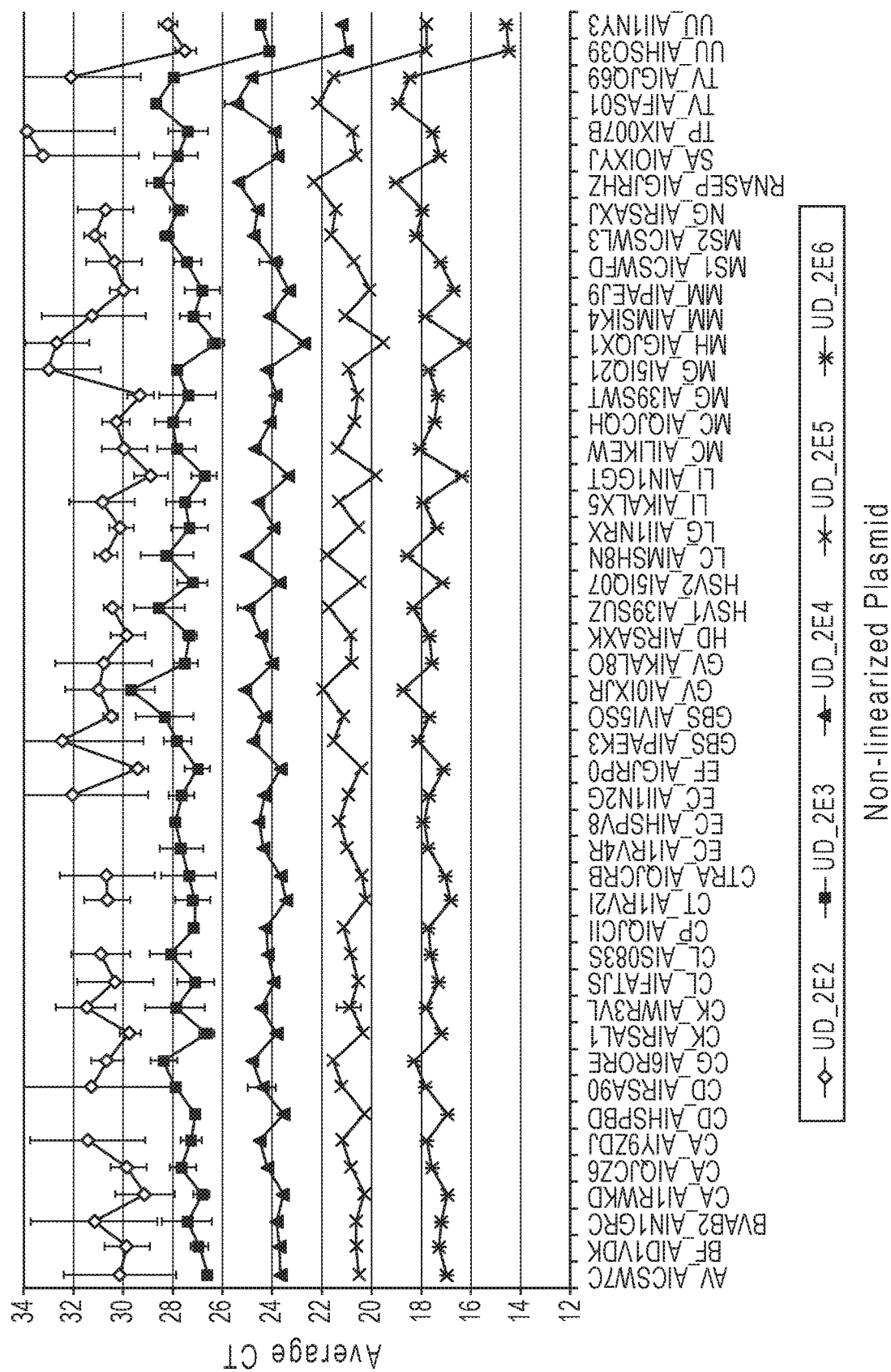
FIG. 3A and FIG. 3B depict graphical results for the average Ct values for 34 different TaqMan assays (see Table 3 for list) using either non-linearized control superplasmid DNA (FIG. 3A), as provided herein, or linearized control superplasmid DNA (FIG. 3B), as provided herein, as the nucleic acid sample. Non-linearized and linearized DNA was provided in each reaction at varying concentrations, as indicated ($2 \times 10^2$ to $2 \times 10^6$).
Figure 3B:
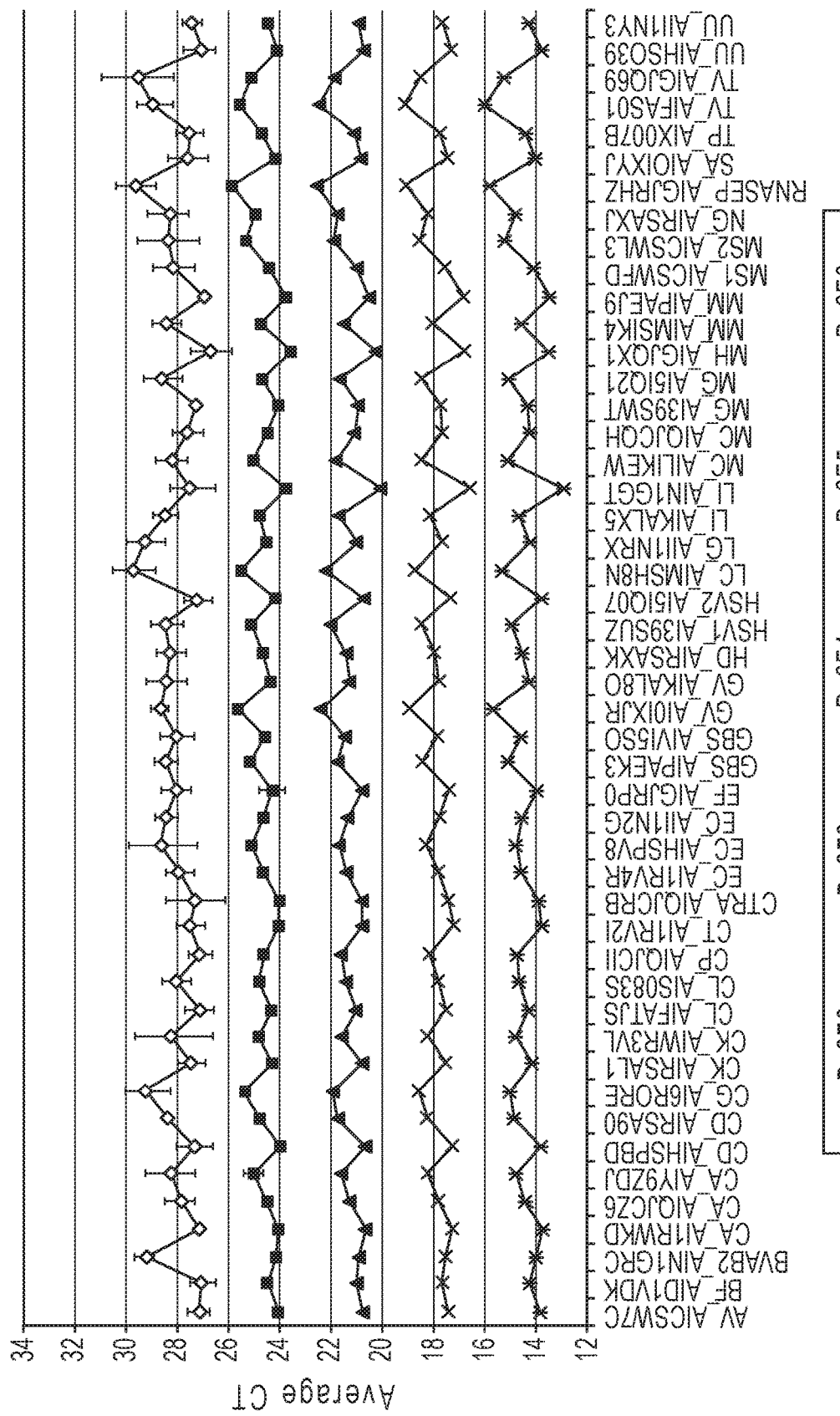

Reactions using supercoiled control plasmid were also compared to those using linearized control plasmid. Superplasmid DNA (comprising the control nucleic acid molecule directed to the panel of 34 assays listed in Table 3) was extracted and prepared as described above. Plasmid preparations were then divided into two portions and one of the portions was linearized by enzyme digestion as describe above while the other portion was mock-digested, using buffer and no digestion enzyme. Both the linearized and the non-linearized (supercoiled) superplasmids were serially diluted to $2 \times 10^2$-$2 \times 10^6$ copies/µl and PCR reactions for both samples was performed as described above for the 34 assay panel used on TaqMan™ OpenArray plates. Amplification of the linearized (FIG. 3B) control plasmid resulted in amplifications reactions with lower Ct values and increased replicate precision when compared to the supercoiled (non-linearized) control plasmids (FIG. 3A). This was particularly observed at lower DNA concentrations. On average, a 2.5 to 3 Ct difference was observed between the linearized plasmid samples and the non-linearized samples when compared at the same concentrations.

Example 2—Nucleic Acid Extraction Control

For the extraction control, the same control nucleic acid molecule that was synthesized for the amplification control, as described above, was cloned into a yeast shuttle vector (pYES2_CT_A307 from Invitrogen) and yeast competent cells were transformed with the resulting shuttle vector containing the control nucleic acid molecule insert. The transformed yeast cells were grown, inactivated, numerated, and lyophilized to $1 \times 10^6$ cells/pellet. Nucleic acid extractions were performed on the reconstituted yeast cells transformed with the control nucleic acid molecule using modified MagMax™ DNA Multi-Sample Ultra Kit reagents and KingFisher™ Flex Purification instrument according to the manufacturer's instructions (Applied Biosystems and Thermo Scientific, Thermo Fisher Scientific), with the exception that an additional cell lysis step using proteinase K was included prior to extraction. The extracted nucleic acid from the yeast cells underwent digital PCR (dPCR) and quantitative PCR (qPCR) screening with the TaqMan™ assays listed in Table 3 to evaluate recovery of the extraction control superplasmid DNA.

Figure 4:
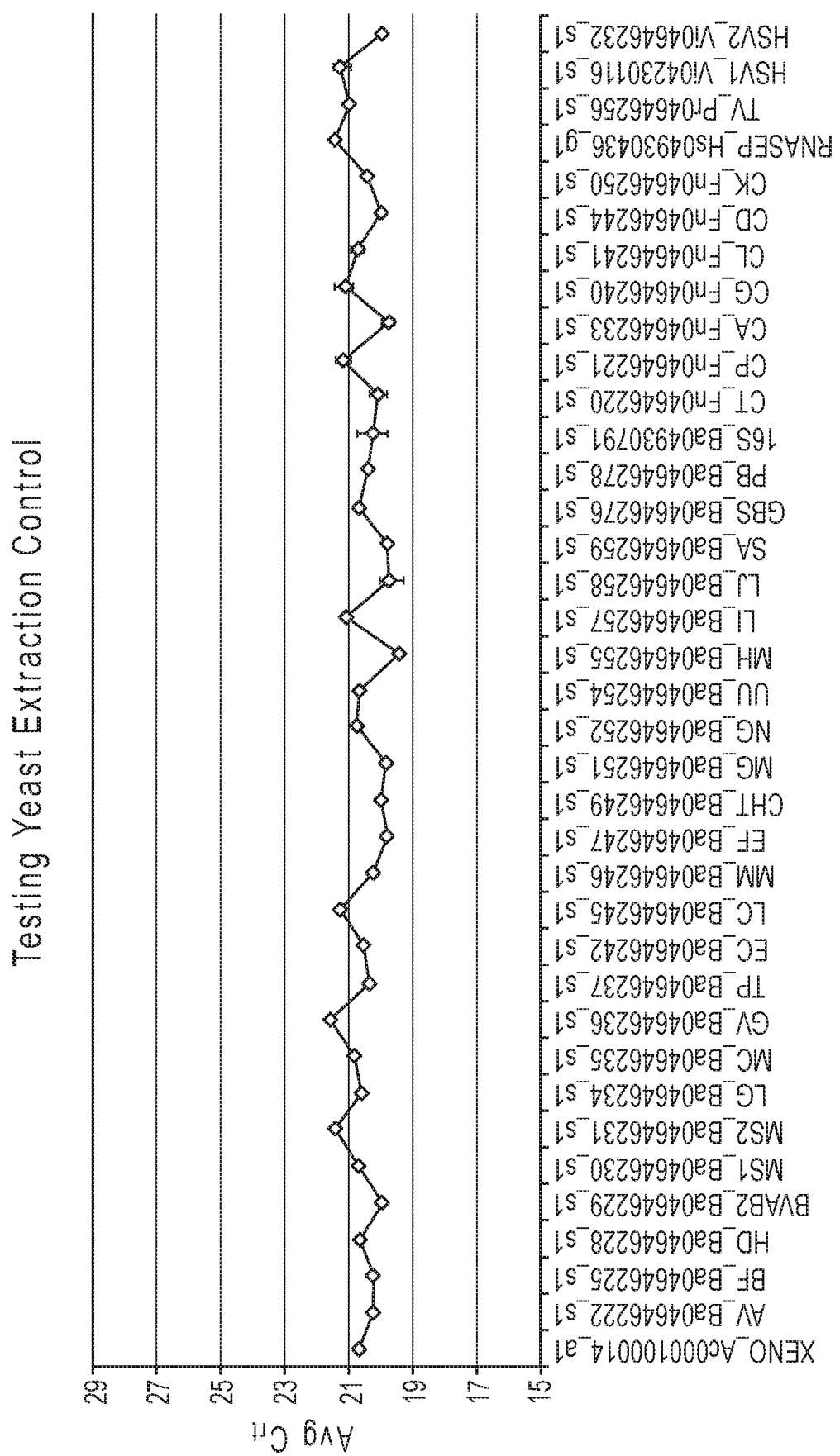
FIG. 4 depicts graphical results for the average Ct values for 34 different TaqMan assays (see Table 3) using superplasmid DNA, as provided herein, extracted from a control sample comprising host yeast cells transformed with the superplasmid ($1 \times 106$ cells/lyophilized pellet) containing a control nucleic acid molecule comprising a plurality of different target sequences.

For qPCR, 2.5 µl of eluted extraction control DNA was mixed with 2.5 µl of TaqMan™ OpenArray™ Real-Time PCR Master Mix and then added to each subarray in which all the assays were spotted on each subarray. For dPCR, the eluted extraction control DNA was diluted based on the Ct values from qPCR to target the optimal final concentration range of 200-2000 copies/µl. Duplex dPCR was run using FAM based target-specific assay and VIC based RNaseP or Xeno assay. 1 ul sample was added to 16 µl dPCR reaction containing master mix and assays. The dPCR mixture was loaded onto a dPCR chip and then thermal cycling was performed. After thermal cycling, the DNA chip was read on QuantStudio 3D Digital PCR System. Both the qPCR assay Ct values and the plasmid copy number determined by dPCR demonstrated that good plasmid recovery and reproducibility was achieved with the extraction control comprising the superplasmid (FIG. 4).

What is claimed is:

1. A method for simultaneous amplification of a first nucleic acid target sequence in a first sample including a control nucleic acid molecule comprising a plurality of different target sequences including the first target sequence, and in a second sample suspected of comprising a test sequence identical to the first target sequence or its complement, the method comprising:
   subjecting both the first sample and the second sample, in separate reaction volumes, to an amplification reaction mixture, the amplification reaction mixture comprising
      a pair of amplification primers configured to enable amplification of the first target sequence of the control nucleic acid molecule in the first sample to thereby form a first sample amplicon, and configured to enable amplification of the test sequence of the second sample to thereby form a second sample amplicon, wherein the first sample amplicon and the second sample amplicon are identical in size and sequence, and
      a detectably labeled probe designed to be specific for a portion of the first target sequence and a portion of the test sequence;
   simultaneously forming the first sample amplicon corresponding to the first target sequence and the second sample amplicon corresponding to the test sequence in the respective separate reaction volumes of the first and second samples; and
   determining the presence of the first sample amplicon and the second sample amplicon in the separate reaction volumes of the first and second samples using the detectably labeled probe,
   wherein the second sample omits the control nucleic acid molecule; and wherein the plurality of different target sequences comprises SEQ ID NOs:1-34, or their respective complements.

2. The method of claim 1, wherein the control nucleic acid molecule contains at least ten different target sequences.

3. The method of claim 1, wherein the plurality of different target sequences is derived from genomic or transcriptomic sequences of different microorganisms.

4. The method of claim 1, wherein the control nucleic acid molecule is a DNA plasmid.

5. The method of claim 4, wherein the plasmid is circularized.

6. The method of claim 4, wherein the plasmid is linearized.

7. The method of claim 4, wherein the plasmid comprises at least one unique restriction site.

8. The method of claim 1, wherein the separate reaction volumes are at different sites or in different reaction vessels on a solid support.

9. The method of claim 8, wherein the solid support is a multi-well plate or an array.

10. The method of claim 1, wherein the first target sequence comprises a sequence selected from the group consisting of SEQ ID NOs:1-34, or its complement.

11. The method of claim 1, wherein the control nucleic acid molecule comprises a portion of a 3' flanking sequence, a portion of a 5' flanking sequence, or both, for at least one of the target sequences.

12. The method of claim 11, wherein the control nucleic acid molecule comprises a portion of a 3' flanking sequence, a portion of a 5' flanking sequence, or both, for each of the target sequences included in the control nucleic acid molecule.

13. The method of claim 11, wherein the portion of the 3' flanking sequence and/or the portion of the 5' flanking sequence is between 15 and 200 nucleotides in length.

14. The method of claim 1, wherein the control nucleic acid further comprises a xeno sequence.

15. The method of claim 14, wherein the xeno sequence is 100-200 nucleotides in length.

16. The method of claim 1, wherein the control nucleic acid molecule is a double stranded nucleic acid molecule.

17. A method for simultaneous amplification of a first nucleic acid target sequence in a first sample including a double stranded control nucleic acid molecule comprising a plurality of different target sequences including the first target sequence, and in a second sample suspected of comprising a test sequence identical to the first target sequence or its complement, the method comprising:

subjecting both the first sample and the second sample, in separate reaction volumes, to an amplification reaction mixture, the amplification reaction mixture comprising a pair of amplification primers configured to enable amplification of the first target sequence of the control nucleic acid molecule in the first sample to thereby form a first sample amplicon, and configured to enable amplification of the test sequence of the second sample to thereby form a second sample amplicon, wherein the first sample amplicon and the second sample amplicon are identical in size and sequence, and a detectably labeled probe designed to be specific for a portion of the first target sequence and a portion of the test sequence;

simultaneously forming the first sample amplicon corresponding to the first target sequence and the second sample amplicon corresponding to the test sequence in the respective separate reaction volumes of the first and second samples; and determining the presence of the first sample amplicon and the second sample amplicon in the separate reaction volumes of the first and second samples using the detectably labeled probe, wherein the second sample omits the control nucleic acid molecule, wherein the control nucleic acid molecule comprises a portion of a 3' flanking sequence, a portion of a 5' flanking sequence, or both, for at least one of the target sequences, and wherein the portion of the 3' flanking sequence and/or the portion of the 5' flanking sequence is 15 nucleotides or greater in length; and wherein the plurality of different target sequences comprises SEQ ID NOs:1-34, or their respective complements.

18. The method of claim 17, wherein the control nucleic acid molecule contains at least ten different target sequences.

19. The method of claim 17, wherein the plurality of different target sequences is derived from genomic or transcriptomic sequences of different microorganisms.

20. The method of claim 17, wherein the control nucleic acid molecule is a DNA plasmid.

21. The method of claim 20, wherein the plasmid comprises at least one unique restriction site.

22. The method of claim 17, wherein the separate reaction volumes are at different sites or in different reaction vessels on a solid support, and wherein the solid support is a multi-well plate or an array.

23. The method of claim 17, wherein the first target sequence comprises a sequence selected from the group consisting of SEQ ID NOs:1-34, or its complement.

24. The method of claim 17, wherein the control nucleic acid molecule comprises a portion of a 3' flanking sequence, a portion of a 5' flanking sequence, or both, for each of the target sequences included in the control nucleic acid molecule.

25. The method of claim 17, wherein the control nucleic acid further comprises a xeno sequence, and wherein the xeno sequence is 100-200 nucleotides in length.

\* \* \* \* \*